United States Patent
Kimura et al.

(10) Patent No.: US 8,287,485 B2
(45) Date of Patent: Oct. 16, 2012

(54) TREATMENT SYSTEM FOR SURGERY AND CONTROL METHOD OF TREATMENT SYSTEM FOR SURGERY

(75) Inventors: Kenichi Kimura, Hachioji (JP); Manabu Ishikawa, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 613 days.

(21) Appl. No.: 12/361,003

(22) Filed: Jan. 28, 2009

(65) Prior Publication Data
US 2010/0191173 A1    Jul. 29, 2010

(51) Int. Cl.
*A61B 17/20* (2006.01)
(52) U.S. Cl. .................. 604/22; 604/27; 604/67
(58) Field of Classification Search .......... 604/22, 604/27, 65, 67
See application file for complete search history.

(56) References Cited

U.S. PATENT DOCUMENTS

| | | |
|---|---|---|
| 4,971,034 A | 11/1990 | Doi et al. |
| 5,520,638 A | 5/1996 | O'Quinn et al. |
| 6,007,556 A | 12/1999 | Kablik et al. |
| 6,579,255 B2 * | 6/2003 | Kadziauskas et al. .......... 604/35 |
| 6,669,690 B1 * | 12/2003 | Okada et al. .................... 606/40 |
| 7,083,601 B1 | 8/2006 | Cosmescu |
| 2004/0102770 A1 | 5/2004 | Goble |

FOREIGN PATENT DOCUMENTS

| | | |
|---|---|---|
| DE | 3601 118 A1 | 7/1986 |
| JP | Sho 61-164545 | 7/1986 |
| JP | 01-135341 | 5/1989 |
| JP | 05-092007 | 4/1993 |
| JP | 2000-135195 | 5/2000 |
| JP | 2004-298559 | 10/2004 |
| WO | 00/41638 A1 | 7/2000 |

OTHER PUBLICATIONS

International Search Report dated Dec. 15, 2009, (4 pages).

* cited by examiner

*Primary Examiner* — Bhisma Mehta
(74) *Attorney, Agent, or Firm* — Scully, Scott, Murphy & Presser, P.C.

(57) ABSTRACT

A treatment system for surgery includes: a handpiece driving apparatus for supplying electric energy to a handpiece, the handpiece including a treatment portion insertable into a body cavity; a perfusion apparatus for perfusing liquid in the body cavity, the perfusion apparatus being capable of adjusting pressure in the body cavity; and a control circuit for controlling the pressure in the body cavity to a different level in conjunction with an output state of the handpiece driving apparatus and changing a flow rate of the perfusion liquid.

12 Claims, 20 Drawing Sheets

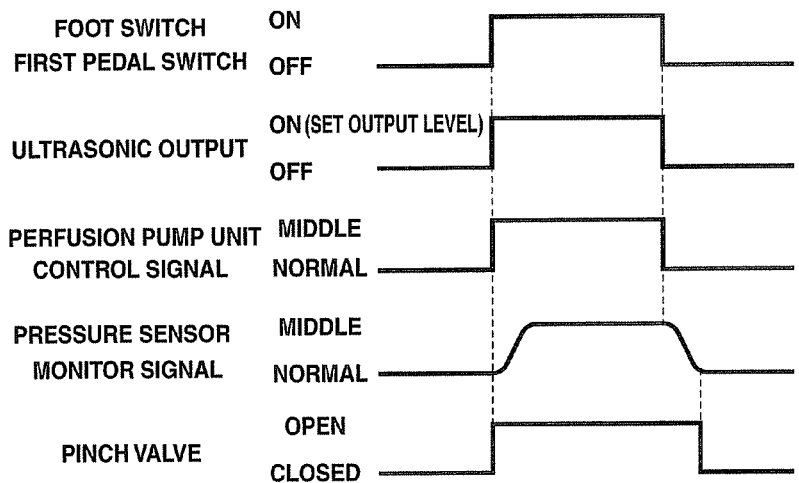
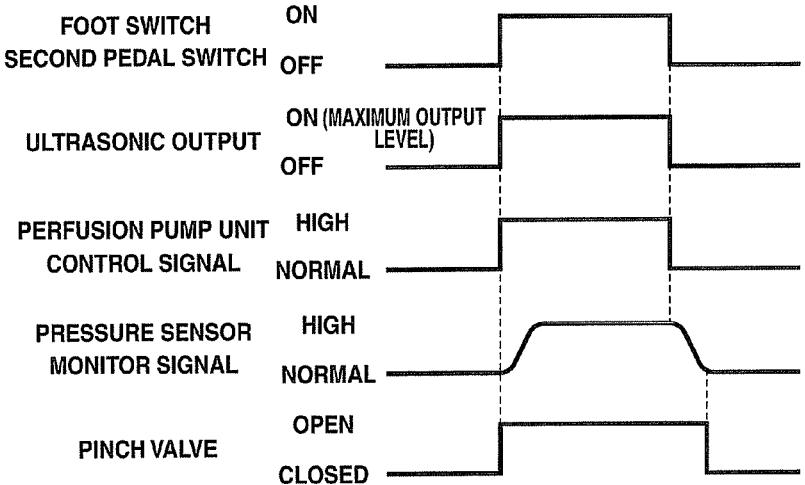

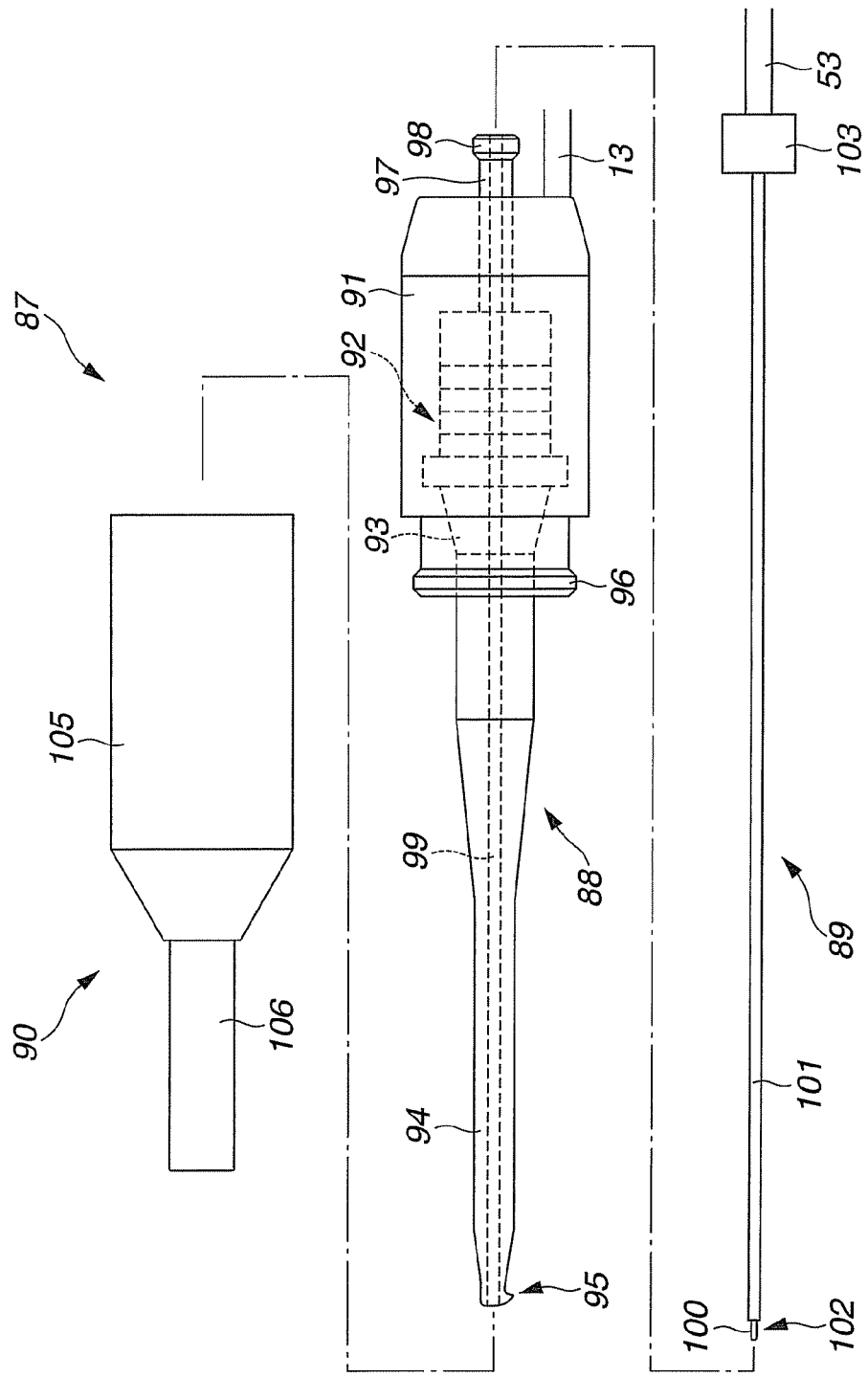

TREATMENT SYSTEM FOR SURGERY AND CONTROL METHOD OF TREATMENT SYSTEM FOR SURGERY

BACKGROUND OF THE INVENTION

1. Field of the Invention

The present invention relates to a treatment system for surgery and a control method of the treatment system for surgery.

2. Description of Related Art

Conventionally, in an endoscopic surgery performed in a body cavity, for example, an arthroscopic surgery in the orthopedic field, treatment has been performed such that a surgical field is ensured by inflating inside of articulation by perfusion liquid such as normal saline or the like using a perfusion pump. As shown in U.S. Pat. No. 5,520,638 or No. 6,007,556, a perfusion pump is controlled to supply perfusion liquid such that pressure in an articulation is kept at a constant level while monitoring the pressure of the liquid in the articulation using a pressure sensor.

In addition, treatment instruments for surgery include a high-frequency treatment instrument for performing treatment by applying high-frequency current to a tissue to be treated.

SUMMARY OF THE INVENTION

A treatment system for surgery according to one aspect of the present invention includes: a handpiece driving apparatus for supplying electric energy to a handpiece, the handpiece including a treatment portion insertable into a body cavity; a perfusion apparatus for perfusing liquid in the body cavity, the perfusion apparatus being capable of adjusting pressure in the body cavity; and a control section for controlling the pressure in the body cavity to a different level in conjunction with an output state of the handpiece driving apparatus and changing a flow rate of the liquid.

A control method of a treatment system for surgery according to one aspect of the present invention is a control method of the treatment system for surgery that includes: a handpiece driving apparatus for supplying electric energy to a handpiece having a treatment portion insertable into a body cavity; and a perfusion apparatus capable of adjusting pressure in the body cavity. The control method includes: perfusing liquid in the body cavity with the perfusion apparatus; and controlling the pressure in the body cavity to a different level in conjunction with an output state of the handpiece driving apparatus and changing a flow rate of the liquid.

BRIEF DESCRIPTION OF THE DRAWINGS

FIGS. 7A to 7E are time charts showing actions of a handpiece driving apparatus and the perfusion apparatus.

FIGS. 8A to 8E are time charts showing the actions of the handpiece driving apparatus and the perfusion apparatus.

FIGS. 17A to 17E and FIGS. 18A to 18E are time charts showing the actions of the handpiece driving apparatus and the perfusion apparatus.

FIG. 19 is a configurational view showing a configuration of a handpiece according to a fourth embodiment of the present invention.

DETAILED DESCRIPTION OF THE PREFERRED EMBODIMENTS

Hereinafter a plurality of embodiments of the present invention will be described with reference to the drawings.

First Embodiment

Figure 1:
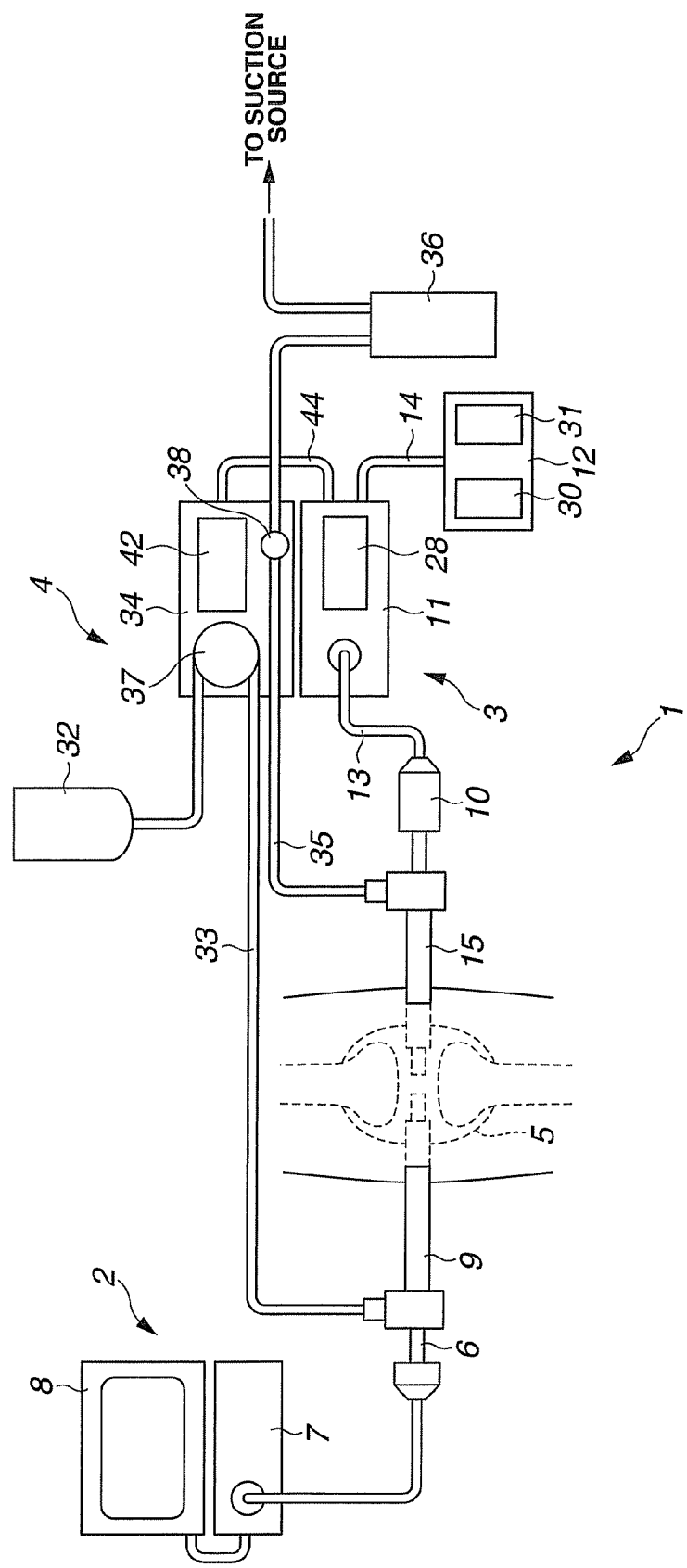
FIG. 1 is a view for describing an overall configuration of a treatment system for surgery according to a first embodiment of the present invention.
Figure 2:
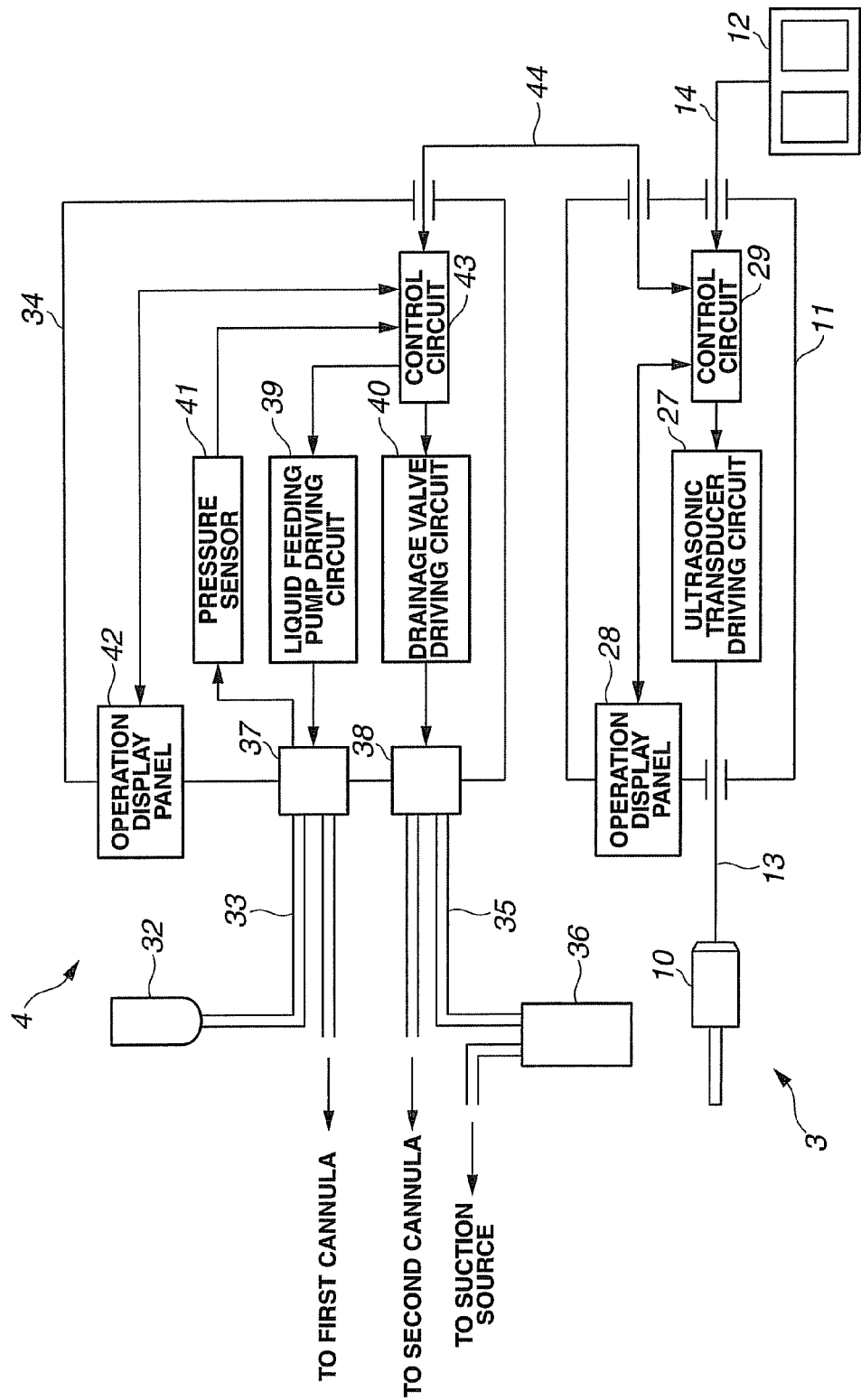
FIG. 2 is a block diagram showing configurations of the treatment apparatus for surgery and a perfusion apparatus according to the first embodiment.
Figure 3:
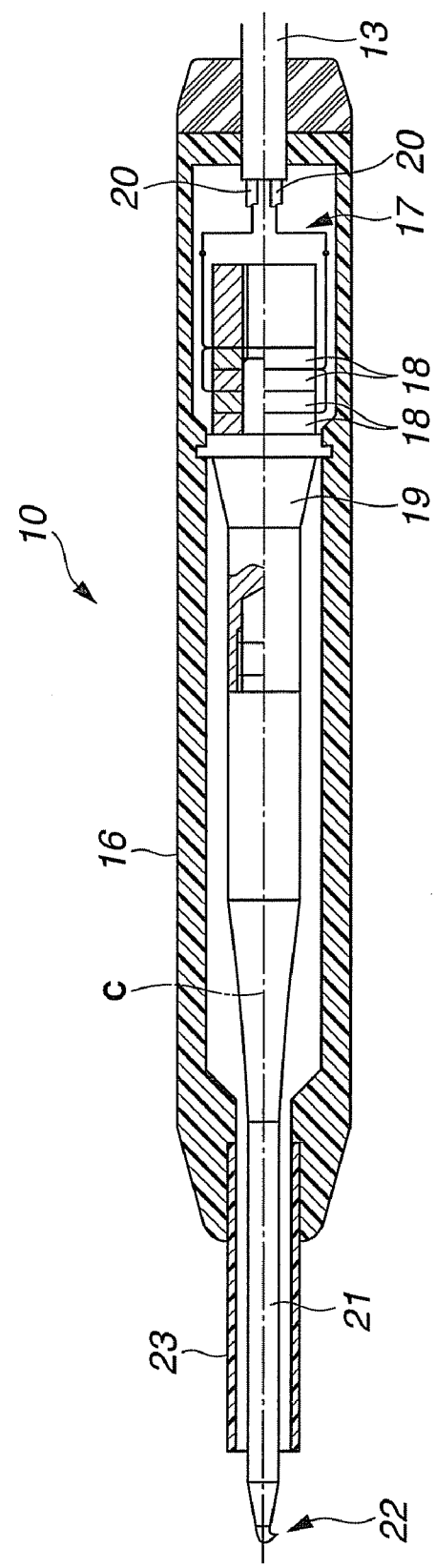
FIG. 3 is a cross-sectional view of a handpiece according to the first embodiment.
Figure 4:
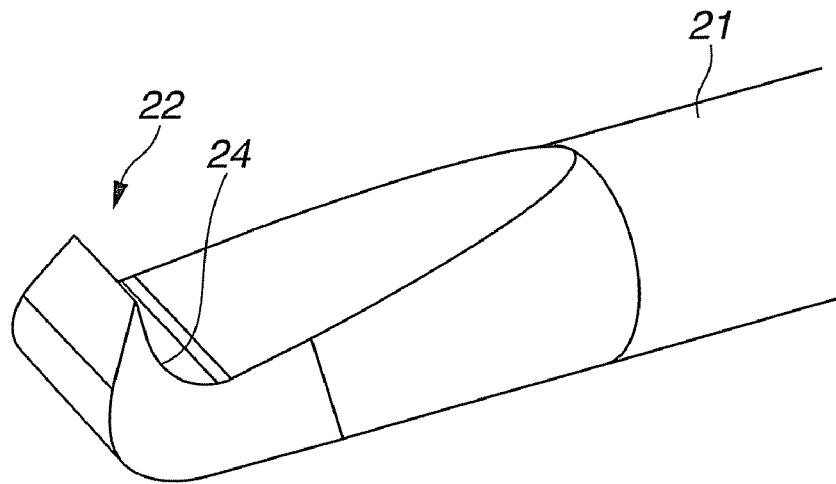
FIG. 4 is a perspective view of a treatment portion of the handpiece according to the first embodiment.
Figure 5:
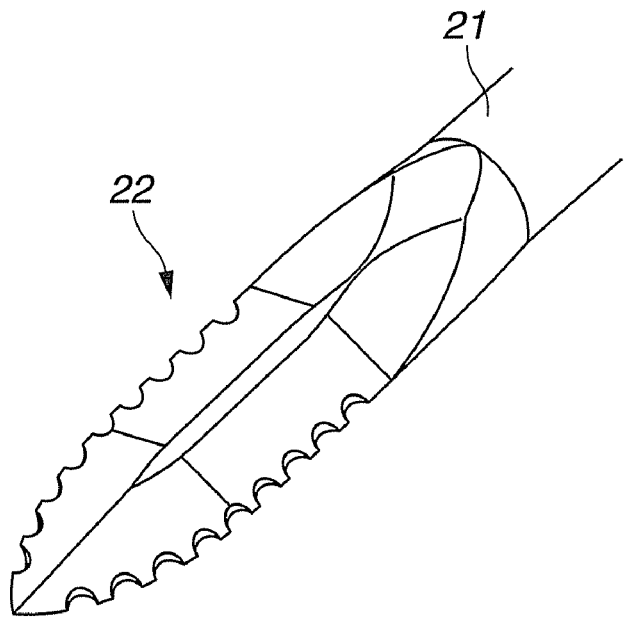
FIG. 5 is a perspective view of another example of the treatment portion of the handpiece.
Figure 6:
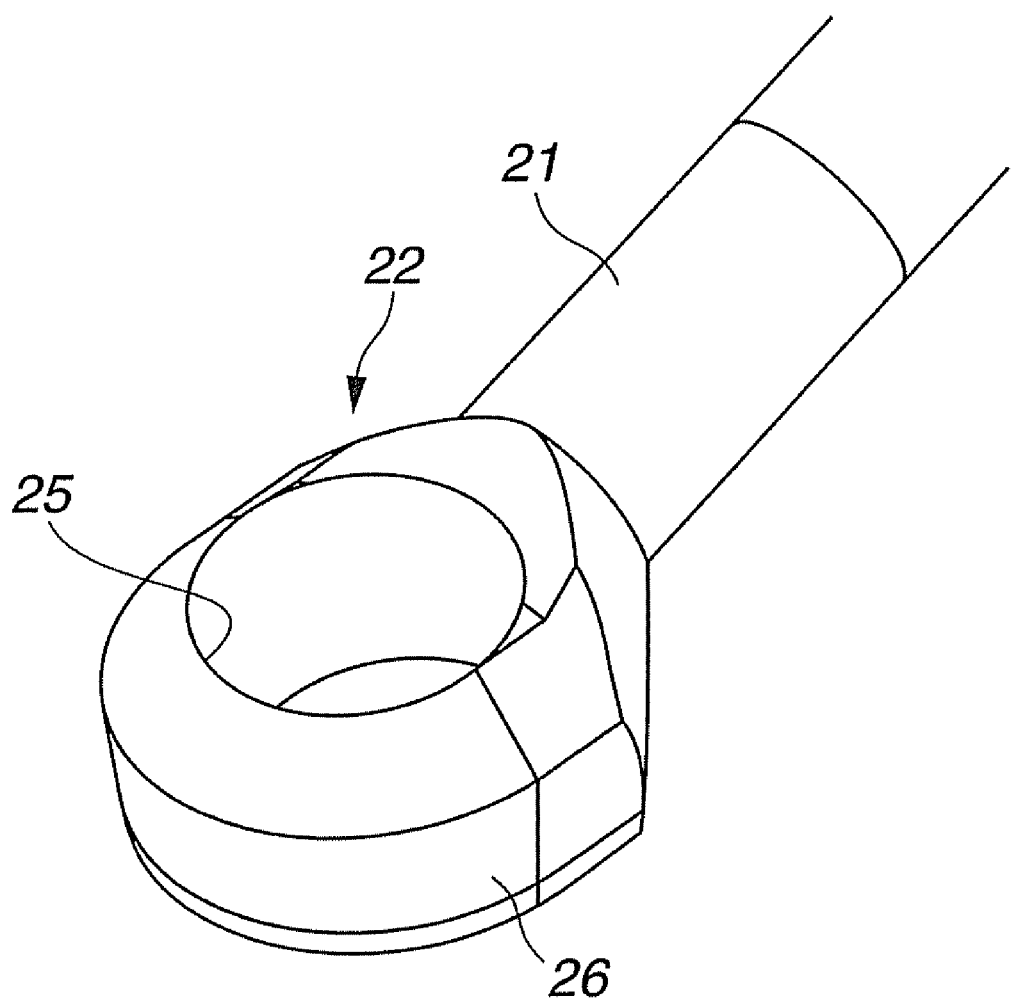
FIG. 6 is a perspective view of yet another example of the treatment portion of the handpiece.

FIGS. 1 to 8 are views for describing a treatment system for surgery according to the first embodiment of the present invention. FIG. 1 is a view for describing an overall configuration of the treatment system for surgery according to the first embodiment. FIG. 2 is a block diagram showing configurations of a treatment apparatus for surgery and a perfusion apparatus according to the first embodiment. FIG. 3 is a cross-sectional view of a handpiece according to the first embodiment. FIG. 4 is a perspective view of a treatment portion of the handpiece according to the first embodiment. FIG. 5 is a perspective view of another example of the treatment portion of the handpiece. FIG. 6 is a perspective view of yet another example of the treatment portion of the handpiece. FIGS. 7A to 7E and FIGS. 8A to 8E are time charts showing actions of a handpiece driving apparatus and the perfusion apparatus.

(Configuration)

As shown in FIG. 1, a treatment system 1 for surgery is configured by including an arthroscope apparatus 2, a treatment apparatus 3 for surgery, and a perfusion apparatus 4.

The arthroscope apparatus 2 includes: an arthroscope 6 for observing inside of an articulation 5 such as a knee, a shoulder, or a hip joint, that is, inside of a body cavity of a patient; a camera device 7 for converting a video from the arthroscope 6 into an electric signal; and a television monitor 8 for displaying the video based on the electric signal from the camera device 7. The arthroscope 6 is inserted in the articulation 5 through a cylindrical first cannula 9 that is inserted in the articulation 5 of the patient.

The treatment apparatus 3 for surgery includes a handpiece 10, a handpiece driving apparatus 11, and a foot switch 12. The handpiece 10 is connected to the handpiece driving apparatus 11 through an output connection cable 13. The foot switch 12 is connected to the handpiece driving apparatus 11 through a switch connection cable 14. The handpiece 10 is inserted into the articulation 5 through a cylindrical second cannula 15 that is inserted in the articulation 5.

As shown in FIG. 3, the handpiece 10 is provided on a rear end side thereof with an approximately cylindrical case 16. In the case 16 is fixed an ultrasonic transducer (in this embodiment, bolt-clamped Langevin transducer: BLT) 17 for generating ultrasonic vibration.

The ultrasonic transducer 17 is provided with a plurality of, four in this embodiment, ring-shaped piezoelectric elements 18 for converting electric power supplied from the handpiece driving apparatus 11 into ultrasonic vibration. On a distal end side of the piezoelectric elements 18 is provided a horn 19 for amplifying ultrasonic vibration generated by the piezoelectric elements 18. The horn 19 is made of a metallic material such as titanium, duralumin, stainless steel, or the like. The piezoelectric elements 18 are connected with a conductive wire 20 in the output connection cable 13 such that electric power for ultrasonic driving is supplied to the piezoelectric elements 18. The output connection cable 13 is extended from a rear end side of the case 16.

On the distal end side of the horn 19 is mounted an ultrasonic probe 21 for transmitting ultrasonic vibration amplified by the horn 19. The horn 19 and the ultrasonic probe 21 are fixed to each other by screw fastening or the like as shown in the partial cross section in FIG. 3.

Like the horn 19, the ultrasonic probe 21 is made of a metallic material such as titanium, duralumin, stainless steel, or the like. On the distal end side of the ultrasonic probe 21 is formed a treatment portion 22 for treating a living tissue. A cylindrical sheath 23 for covering the ultrasonic probe 21 is integrally provided on the distal end side of the case 16.

The treatment portion 22 has a hook shape as shown in FIG. 4. In this embodiment, a working surface 24 on which the living tissue is resected or shaved is formed on a hook-shaped portion generally vertically with respect to a central axis C of the ultrasonic probe 21.

Note that the shape of the treatment portion 22 is not limited to the above-described shape, and may be formed in a shape shown in FIG. 5 or FIG. 6. The treatment portion 22 shown in FIG. 5 has a generally flat knife shape with a sharp tip end. In addition, around the treatment portion 22 shown in FIG. 5 are formed a plurality of semicircular depressions at regular intervals along a knife-shaped edge. The treatment portion 22 shown in FIG. 6 has a shape of a ring curette. The treatment portion 22 shown in FIG. 6 has an edge 25 for resecting and shaving the living tissue that is formed on an inner peripheral distal end side of the ring 26.

As shown in FIG. 2, the handpiece driving apparatus 11 for supplying electric energy to the handpiece 10 is provided with an ultrasonic transducer driving circuit 27 for driving the ultrasonic transducer 17 of the handpiece 10, an operation display panel 28 for setting and displaying output level of ultrasonic output, and a control circuit 29. The ultrasonic transducer driving circuit 27 is connected with the handpiece 10 through the output connection cable 13. The control circuit 29 as a control section is connected with the foot switch 12 through the switch connection cable 14. In addition, the control circuit 29 is connected with the ultrasonic transducer driving circuit 27 and the operation display panel 28. Operation signals from the foot switch 12 and the operation display panel 28 are inputted to the control circuit 29, and the control circuit 29 controls the ultrasonic transducer driving circuit 27 and the operation display panel 28.

The foot switch 12 is provided with a first pedal switch 30 and a second pedal switch 31.

As shown in FIG. 1, the perfusion apparatus 4 includes a bag-like liquid source 32 in which perfusion liquid such as normal saline is stored, a liquid feeding tube 33 one end of which is connected to the liquid source 32, a perfusion pump unit 34, a drainage tube 35, a suction bottle 36 to which one end of the drainage tube 35 is connected, and a suction source connected to the suction bottle 36. The liquid feeding tube 33 as a liquid feeding conduit has the other end connected to the first cannula 9, thereby sending the perfusion liquid into the articulation 5 through a bore, that is, an insertion path of the first cannula 9. Furthermore, the drainage tube 35 as a drainage conduit has the other end connected to the second cannula 15, thereby discharging the perfusion liquid from inside of the articulation 5 through the bore of the second cannula 15.

As shown in FIGS. 1 and 2, the perfusion pump unit 34 is provided with a roller pump 37 as a liquid feeding pump. The liquid feeding tube 33 is attached to the roller pump 37 and the perfusion liquid is pumped out. In addition, the perfusion pump unit 34 is provided with a pinch valve 38 as a drainage valve. To the pinch valve 38 is attached the drainage tube 35. Opening and closing the pinch valve 38 enables and disables the flow of the perfusion liquid in the drainage tube 35.

In addition, as shown in FIG. 2, the perfusion pump unit 34 is provided with: a liquid feeding pump driving circuit 39 for driving the roller pump 37; a drainage valve driving circuit 40 for driving the pinch valve 38; a pressure sensor 41 for monitoring pressure in the articulation 5; an operation display panel 42 for setting and displaying the pressure level in the articulation 5; and a control circuit 43 as a control section.

The liquid feeding pump driving circuit 39 is connected to the roller pump 37 to send a drive signal to the roller pump 37. The drainage valve driving circuit 40 is connected to the pinch valve 38 to send drive signals for opening and closing to the pinch valve 38. Moreover, the pressure sensor 41 is connected to the liquid feeding tube 33 and indirectly monitors the pressure in the articulation 5.

The control circuit 43 is connected with the liquid feeding pump driving circuit 39, the drainage valve driving circuit 40, the operation display panel 42, and the pressure sensor 41. The operation signal from the operation display panel 42 and a pressure monitor signal from the pressure sensor 41 are inputted to the control circuit 43, and the control circuit 43 controls the liquid feeding pump driving circuit 39, the drainage valve driving circuit 40, and the operation display panel 42. The perfusion apparatus 4 having the above-described configuration can perfuse the perfusion liquid in the articulation 5 and adjust the pressure in the articulations 5.

The control circuit 29 of the handpiece driving apparatus 11 and the control circuit 43 of the perfusion pump unit 34 are connected to each other through a communication cable 44 such that various signals can be transmitted bi-directionally.

(Working)

Description will be made on the case where the operator treats a living tissue using the treatment system 1 for surgery.

First, the arthroscope apparatus 2, the treatment apparatus 3 for surgery, and the perfusion apparatus 4 are placed in a surgery room, as shown in FIG. 1. That is, the arthroscope 6 is inserted in the articulation 5 such as the knee, the shoulder, or the hip joint of the patient through the first cannula 9. Furthermore, the handpiece 10 is inserted in the articulation 5 through the second cannula 15. One end of the liquid feeding tube 33 is connected to the first cannula 9 and one end of the drainage tube 35 is connected to the second cannula 15.

Perfusion in the articulation 5 is then performed by the perfusion apparatus 4. First, the pressure level in the articulation 5 is set to "Normal" (approximately 40 mmHg in this case) using the operation display panel 42 of the perfusion pump unit 34. Then, the operation signal from the operation display panel 42 is inputted to the control circuit 43, and thereby the roller pump 37 is driven. At this time, the monitor signal from the pressure sensor 41 is sent to the control circuit 43, and thereby the control circuit 43 controls the driving of the roller pump 37 such that the pressure in the articulation 5 achieves the level set through the operation display panel 42. Note that the pinch valve 38 is in a closed state at this time. As a result, inside of the articulation 5 becomes an inflated state by the constant pressure due to the perfusion liquid such as normal saline, which enables excellent observation with the arthroscope 6.

Next, treatment is performed on a living tissue using the treatment apparatus 3 for surgery. First, the output level of ultrasonic output (for example, 70%) is set. The output level setting is performed by the operator's operation of the operation display panel 28 of the handpiece driving apparatus 11.

Then the operator brings the treatment portion 22 of the handpiece 10 into contact with the region to be treated of the living tissue. When the operator turns on the foot switch 12, the operation signal from the foot switch 12 is inputted to the control circuit 29 and the ultrasonic transducer 17 is driven by the ultrasonic transducer driving circuit 27. As a result, the ultrasonic probe 21 generates ultrasonic vibration, and thereby the living tissue which is in contact with the treatment portion 22 is treated with the ultrasonic vibration. When the operator turns on the first pedal switch 30 of the foot switch 12, the control circuit 29 controls the ultrasonic transducer driving circuit 27 such that the ultrasonic transducer 17 is driven at the output level (for example, 70%) set through the operation display panel 28. In addition, when the operator turns on the second pedal switch 31 of the foot switch 12, the control circuit 29 controls the ultrasonic transducer driving circuit 27 such that the ultrasonic transducer 17 is driven at the maximum output level (100%). In this case, the ultrasonic transducer 17 is driven by constant current control, which maintains the amplitude of the ultrasonic vibration in the treatment portion 22 constant.

Note that the handpiece 10 having the treatment portion 22 in the shape shown in FIG. 4 or FIG. 6 is suitable for shaving an articular cartilage. In addition, the handpiece 10 having the treatment portion 22 in the shape shown in FIG. 5 is suitable for resecting an articular capsule and an articular labrum.

Note that, when treating the living tissue with the treatment apparatus 3 for surgery, if the treatment portion 22 of the ultrasonic probe 21 which generates ultrasonic vibration contacts a fatty soft tissue or the like, the soft tissue or the like is emulsified by cavitation generated by the treatment portion 22. As a result, white turbidity appears in the perfusion liquid, and in some cases it is difficult to ensure a field of view of the arthroscope 6. Note that, as the output level of the ultrasonic output becomes higher, larger cavitation is generated. As a result, the white turbidity in the perfusion liquid is increased.

In the present embodiment, the control circuit 29 of the handpiece driving apparatus 11 and the control circuit 43 of the perfusion pump unit 34 are connected to each other through the communication cable 44 which can bi-directionally transmit signals. The control circuit 29 sends to the control circuit 43 the signal indicating the output state of the ultrasonic output. In response to the signal, the control circuit 43 controls the liquid feeding pump driving circuit 39 and the drainage valve driving circuit 40 in conjunction with the output state of the ultrasonic output. That is, the control circuit 43 controls the pressure in the articulation to different levels in conjunction with the output state of the handpiece driving apparatus 11 and changes the flow rate of the perfusion liquid. As a result, the pressure level of when the handpiece 10 is driven is higher than the pressure level of when the handpiece 10 is not driven. Furthermore, the flow rate of the perfusion liquid of when the handpiece 10 is driven is larger than the flow rate of when the handpiece 10 is not driven.

FIGS. 7A to 7E and FIGS. 8A to 8E are examples of time charts showing the output state of ultrasonic output and the action of the perfusion pump unit 34. FIGS. 7A to 7E are time charts in the case where the handpiece 10 is driven at a set output level (for example, 70%) by the operation of the first pedal switch 30.

As shown in FIGS. 7A to 7E, when the foot switch 12 is in a turn-off state, the handpiece 10 is not driven, i.e., the ultrasonic output is turned off. At this time, the perfusion pump unit 34 performs control such that the pressure in the articulation 5 achieves a "Normal" pressure level (approximately 40 mmHg) set through the operation display panel 42. At this time, the pinch valve 38 is in a closed state.

Next, when the first pedal switch 30 of the foot switch 12 is turned on, the handpiece 10 is driven at the output level (for example, 70%) set through the operation display panel 28.

In this case, the perfusion pump unit 34 performs control such that the pressure in the articulation 5 achieves the preset "Middle" pressure level (approximately 60 mmHg). At this time, the pinch valve 38 is in an open state. The pressure in the articulation 5 monitored by the pressure sensor 41 achieves "Middle" pressure level after a certain period of time has passed following the turn-on operation of the first pedal switch 30.

Next, when the first pedal switch 30 is turned off, the ultrasonic output is controlled to be in a turn-off state. The perfusion pump unit 34 performs control such that the pressure in the articulation 5 achieves the "Normal" pressure level. The pressure in the articulation 5 monitored by the pressure sensor 41 achieves the "Normal" pressure level after a certain period of time has passed following the turn-off operation of the first pedal switch 30. At the time that the pressure in the articulation 5 monitored by the pressure sensor 41 achieves the "Normal" pressure level, control is performed to close the pinch valve 38.

As described above, while the ultrasonic output is performed, the flow rate of the perfusion liquid increases, since the pressure in the articulation 5 is kept at a high level and the pinch valve 38 is open to actively discharge the liquid. Accordingly, even if the soft tissue or the like is emulsified by the cavitation generated by the treatment portion 22 and the white turbidity thereby appears in the perfusion liquid, the field of view is rapidly restored.

When the articular cartilage is shaved using the handpiece 10 having the treatment portion 22 in the shape shown in FIG. 4 or FIG. 6, shaved pieces are efficiently discharged from the drainage tube 35, which maintains an excellent field of view.

While the ultrasonic output is not performed, tumefaction of the diseased part (articulation 5) after surgery can be reduced, since the pressure in the articulation 5 is kept at a low level. In addition, since the pinch valve 38 is closed, the flow rate of the perfusion liquid is decreased. As a result, the amount of perfusion liquid used in the surgery can be reduced.

FIGS. 8A to 8E are time charts in the case where the handpiece 10 is driven at the maximum output level (100%) by the operation of the second pedal switch 31. In this case, the perfusion pump unit 34 performs control such that the pressure in the articulation 5 achieves preset "High" pressure level (approximately 80 mmHg) while the ultrasonic output is performed. Other actions are the same as those shown in FIGS. 7A to 7E. That is, in the case shown in FIGS. 8A to 8E where the output level of ultrasonic output is higher than that in the case shown in FIGS. 7A to 7E, the perfusion amount during the ultrasonic output is more increased than in the case shown in FIGS. 7A to 7E. Accordingly, even in the state where the ultrasonic output is increased and the white turbidity in the perfusion liquid thereby increased, the field of view is restored as rapidly as in the case shown in FIGS. 7A to 7E.

(Effect)

As described above, according to the treatment system for surgery of the present embodiment, while the ultrasonic output is performed, the flow rate of the perfusion liquid increases, since the pressure in the articulation 5 is kept at a high level and the pinch valve 38 is open to actively discharge the liquid. As a result, even when white turbidity appears in the perfusion liquid due to the treatment using the handpiece 10, the field of view can be rapidly restored. Furthermore, since the shaved pieces or the like of the living tissue generated by the treatment using the handpiece 10 are efficiently discharged from the drainage tube 35, an excellent field of view can be maintained.

In addition, while the ultrasonic output is not performed, the tumefaction of the diseased part, for example, the articulation 5 after surgery can be reduced, since the pressure in the articulation 5 is kept at a low level.

Second Embodiment

Next, a treatment system for surgery according to the second embodiment of the present invention will be described.

Figure 9:
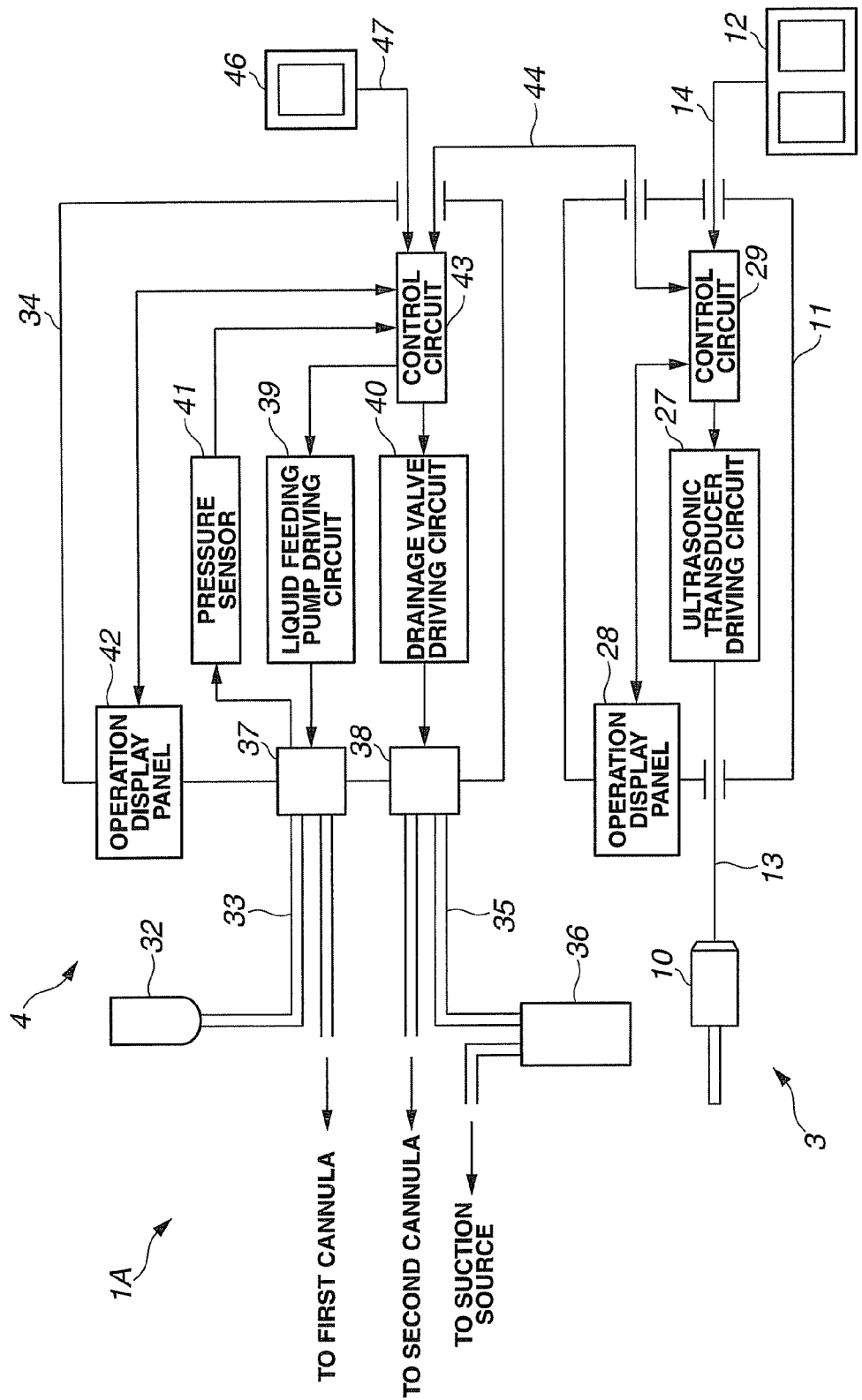
FIG. 9 is a block diagram showing configurations of a treatment apparatus for surgery and a perfusion apparatus according to a second embodiment of the present invention.

FIG. 9 is a block diagram showing configurations of a treatment apparatus for surgery and a perfusion apparatus according to the second embodiment. In FIG. 9, the same components as those in FIG. 2 are attached with the same reference numerals and descriptions thereof will be omitted. Only the parts different from those in the first embodiment will be described.

(Configuration)

As shown in FIG. 9, in the treatment system 1A for surgery according to the present embodiment, the control circuit 43 of the perfusion pump unit 34 is connected with a switch 46 such as a foot switch, through a switch connection cable 47. The treatment system 1A for surgery is configured such that the operation signal from the switch 46 is inputted to the control circuit 43.

The switch 46 is a switch for driving the control circuit 43 so as to cause the control circuit to change the flow rate of the perfusion liquid even in the state where electric energy is not supplied to the handpiece 10.

(Working)

When the switch 46 is turned on, the perfusion pump unit 34 performs control such that the pressure in the articulation 5 achieves the preset "Middle" pressure level (approximately 60 mmHg) or "High" pressure level (approximately 80 mmHg). Furthermore, the perfusion pump unit 34 performs control to open the pinch valve 38. This control keeps the pressure in the articulation 5 at a high level and the pinch valve 38 open to actively discharge the liquid while the switch 46 is turned on. As a result, the flow rate of the perfusion liquid increases.

That is, in the treatment system 1A for surgery according to the present embodiment, even in the state where the ultrasonic output of the handpiece 10 is not performed, the operator can arbitrarily increase the flow rate of the perfusion liquid by operating the switch 46.

When the field of view is not clear due to the floating shaved pieces or the like of the living tissue in the articulation 5, the operator has only to turn on the switch 46, to increase the flow rate of the perfusion liquid thus allowing active liquid discharge, without the ultrasonic output of the handpiece 10.

Note that when the switch 46 as switch means is turned on, the control circuit 43 of the perfusion pump unit 34 may send the operation signal of the switch 46 to the control circuit 29 of the handpiece driving apparatus 11, such that, when the operation signal is inputted, the control circuit 29 may disable turn-on operation by the foot switch 12. That is, when the control circuit 29 receives the operation signal, ultrasonic output is not performed even if the foot switch 12 is turned on. According to this configuration, the field of view can be surely restored without the ultrasonic output of the handpiece 10.

(Effect)

As described above, the present embodiment enables increase in the flow rate of the perfusion liquid, efficient restoration of field of view, and discharge of the shaved pieces or the like of the living tissue, even in the state where the ultrasonic output of the handpiece is not performed.

Third Embodiment

Next, a treatment system for surgery according to the third embodiment of the present invention will be described.

Figure 10:
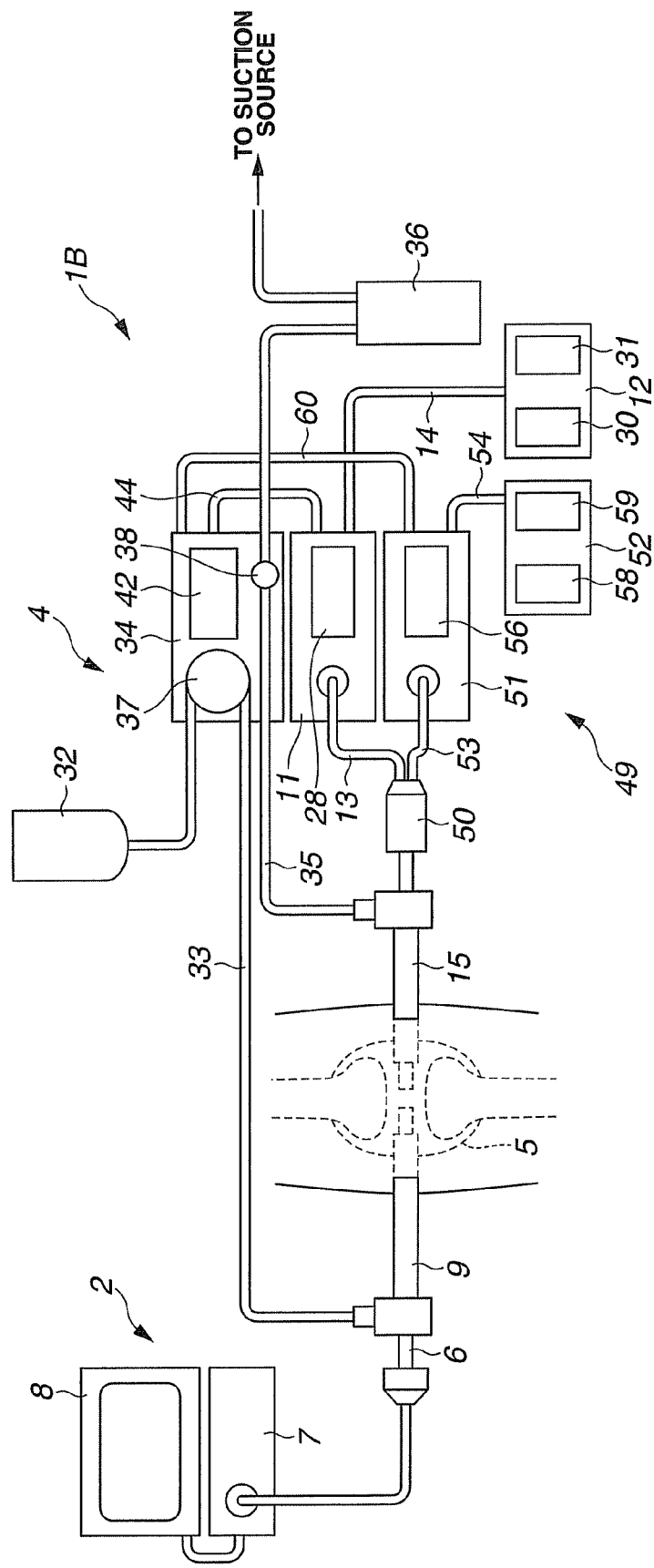
FIG. 10 is a view describing an overall configuration of a treatment system for surgery according to a third embodiment of the present invention.
Figure 11:
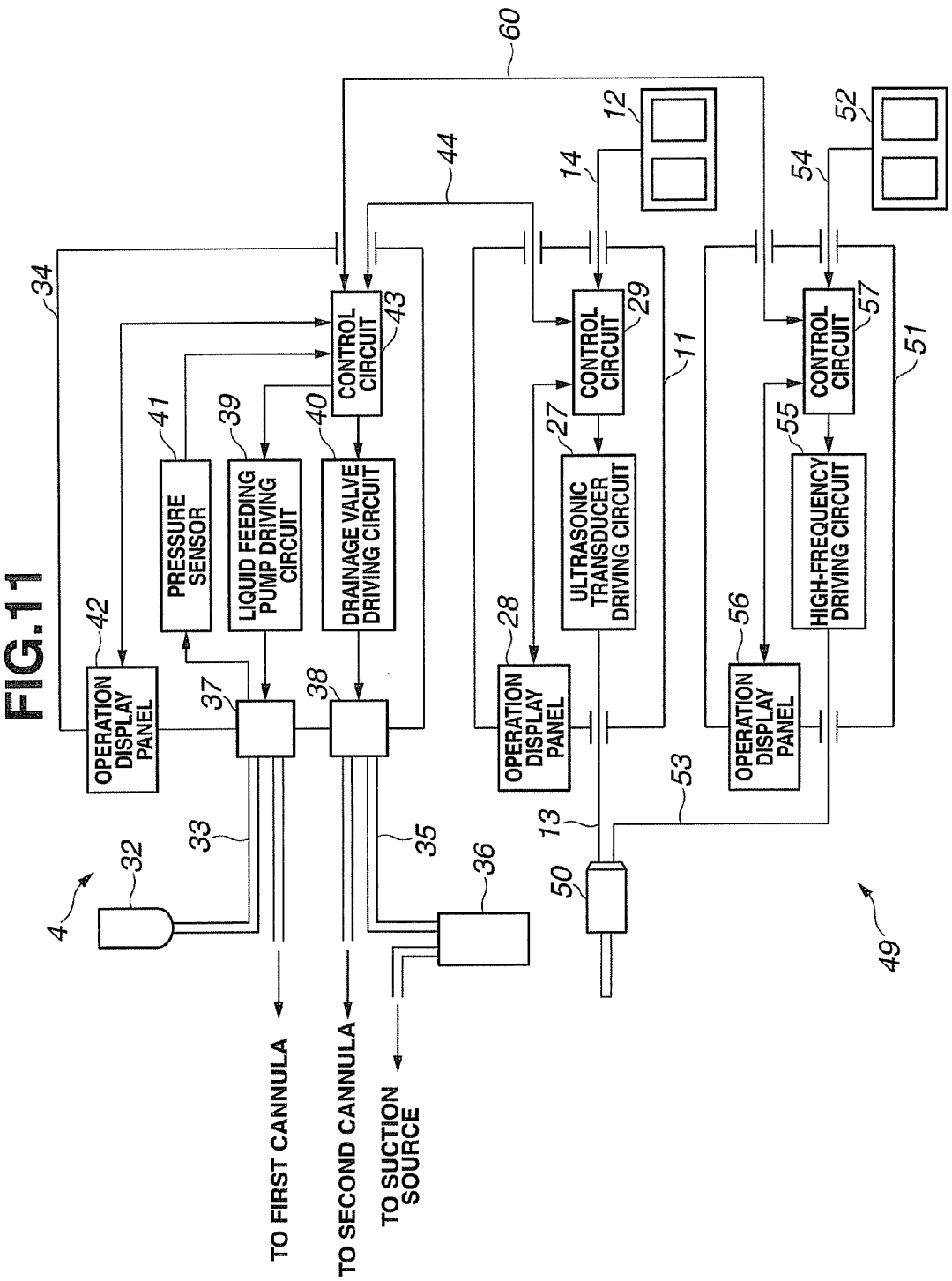
FIG. 11 is a block diagram showing configurations of a treatment apparatus for surgery and a perfusion apparatus according to the third embodiment.
Figure 12:
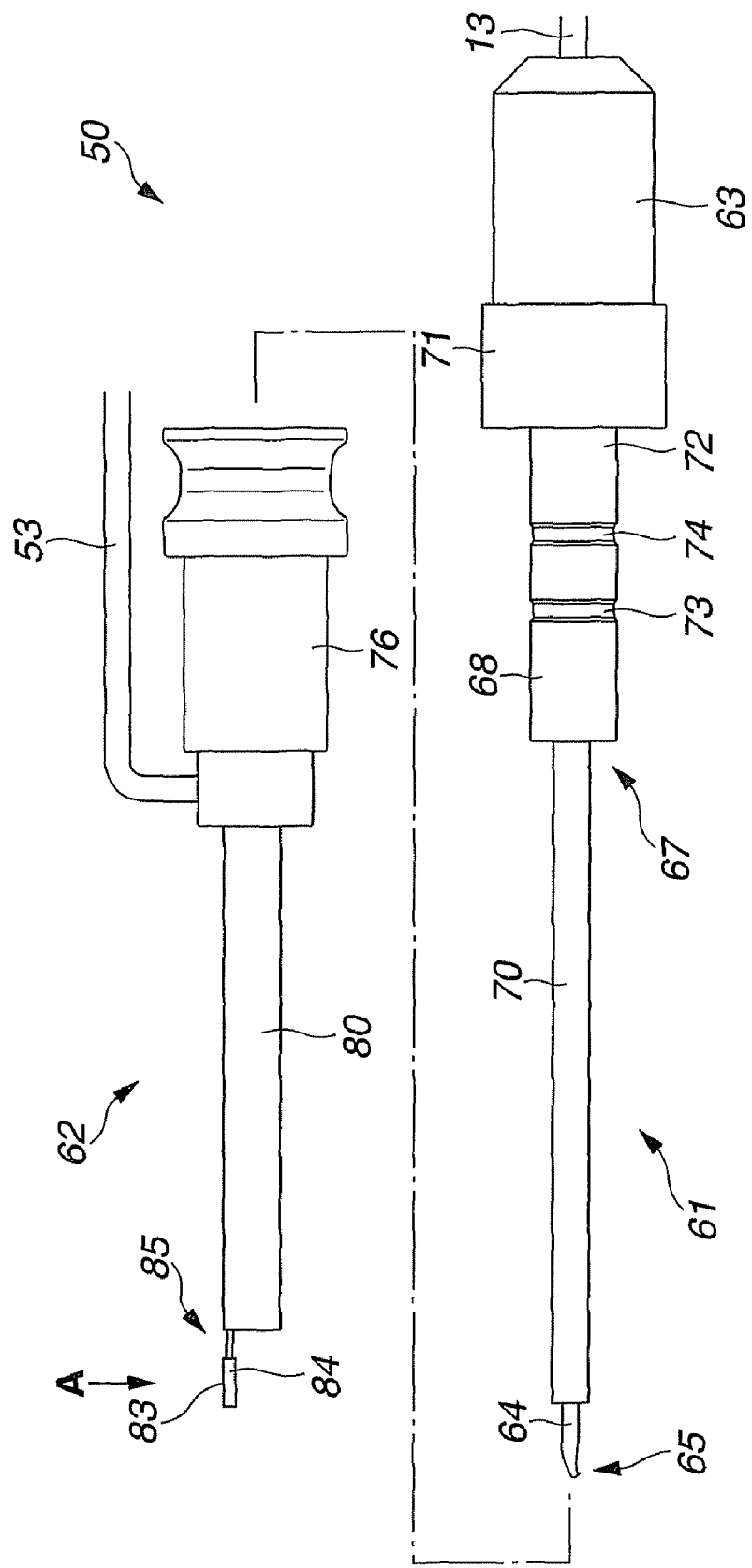
FIG. 12 is a configurational view showing a configuration of a handpiece according to the third embodiment.
Figure 13:
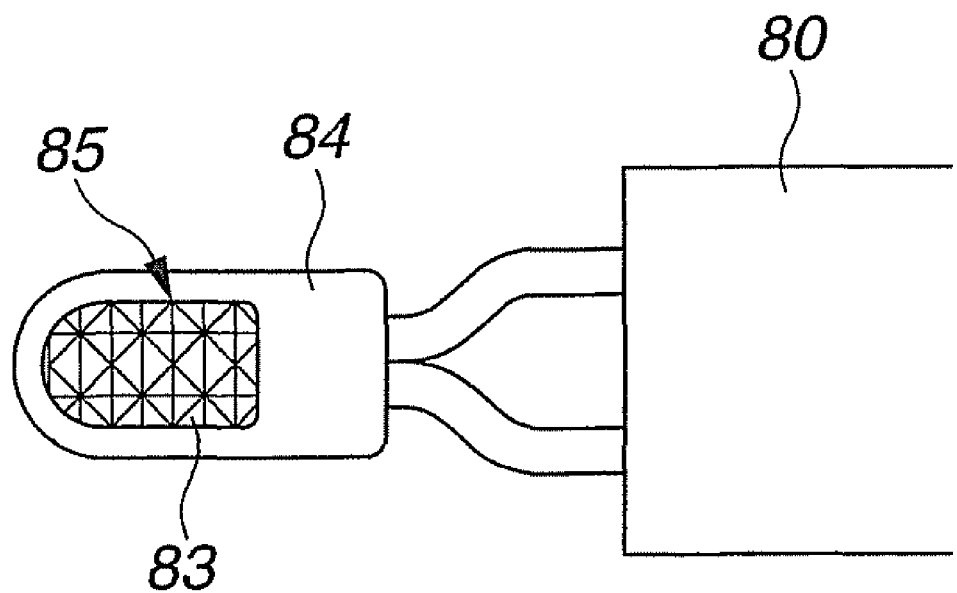
FIG. 13 is a view on arrow A viewed in a direction of the arrow A in FIG. 12.
Figure 14:
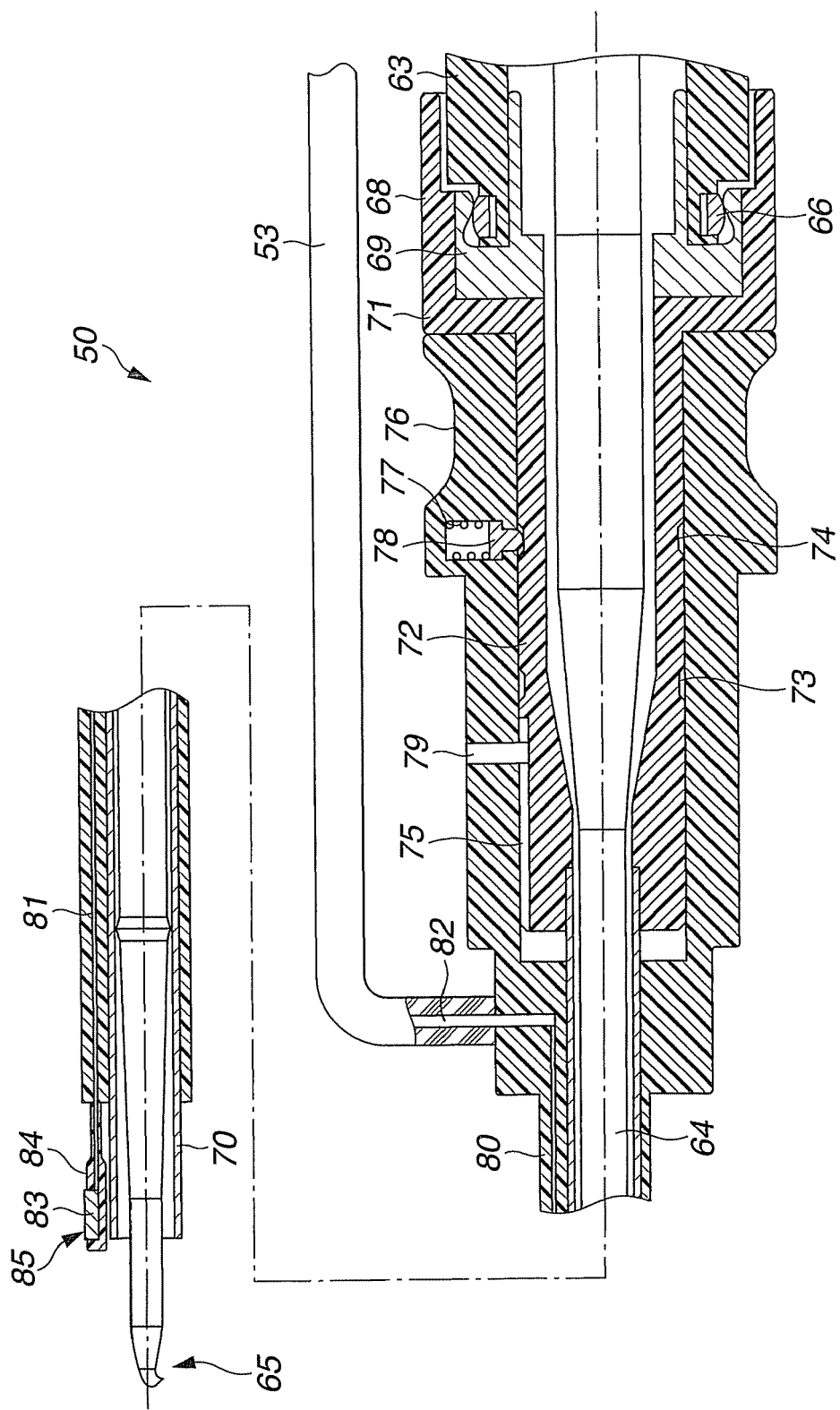
FIG. 14 is a cross-sectional view of the handpiece.
Figure 15:
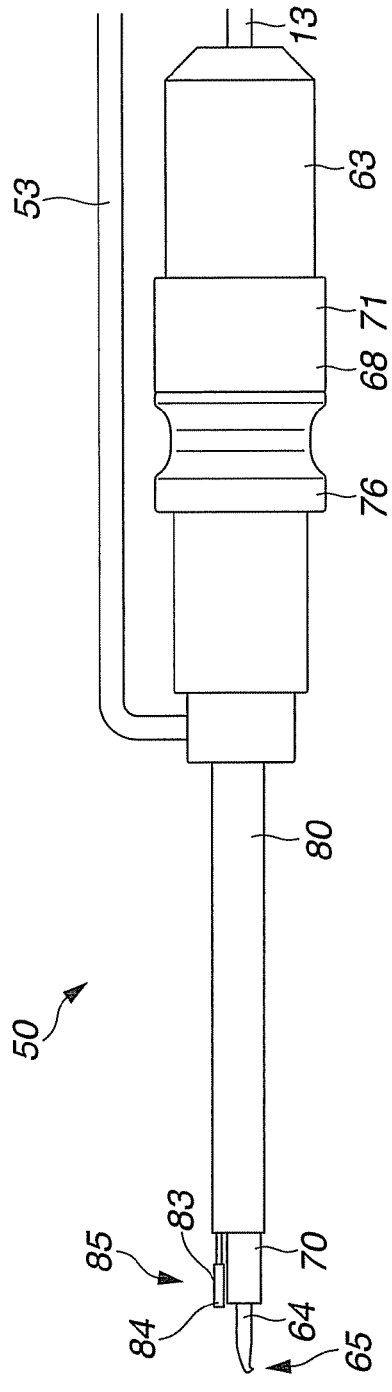
FIGS. 15 and 16 are exterior views of the handpiece.
Figure 16:
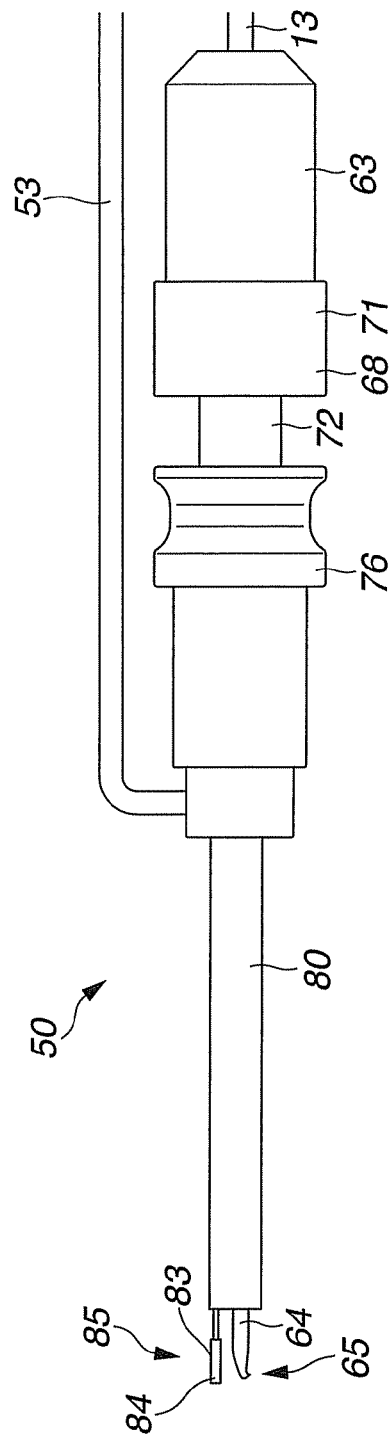

FIGS. 10 to 18 are block diagrams showing configurations of a treatment apparatus for surgery and a perfusion apparatus according to the third embodiment. FIG. 10 is a view for describing an overall configuration of the treatment system for surgery according to the third embodiment. FIG. 11 is a block diagram showing configurations of the treatment apparatus for surgery and the perfusion apparatus according to the third embodiment. FIG. 12 is a configurational view showing configuration of a handpiece according to the third embodiment. FIG. 13 is a view on arrow A viewed in a direction of the arrow A in FIG. 12. FIG. 14 is a cross-sectional view of the handpiece. FIGS. 15 and 16 are exterior views of the handpiece. FIGS. 17A to 17E and FIGS. 18A to 18E are time charts showing actions of the handpiece driving apparatus and the perfusion apparatus. In FIGS. 10 to 18E, the same components as those in FIG. 2 are attached with the same reference numerals and descriptions thereof will be omitted. Only the parts different from the first embodiment will be described.

(Configuration)

As shown in FIG. 10, in a treatment system 1B for surgery according to the present embodiment, a treatment apparatus 49 for surgery includes a handpiece 50, a handpiece driving apparatus 11 as an ultrasonic driving apparatus, a foot switch 12, a handpiece driving apparatus 51 as a high-frequency driving apparatus, and a foot switch 52. The configurations of the handpiece driving apparatus 11 and the foot switch 12 are the same as those in the first embodiment. The handpiece 50 is connected to the handpiece driving apparatus 11 through an output connection cable 13 and also connected to the handpiece driving apparatus 51 through an output connection cable 53. The foot switch 52 is connected to the handpiece driving apparatus 51 through a switch connection cable 54.

As shown in FIG. 11, the handpiece driving apparatus 51 which supplies electric energy to the handpiece 50 is provided with: a high-frequency driving circuit 55 for supplying high-frequency current to the handpiece 50; an operation display panel 56 for setting and displaying an output level of high-frequency output; and a control circuit 57 as a control section. The high-frequency driving circuit 55 is connected with the handpiece 50 through the output connection cable 53. The control circuit 57 is connected with the foot switch 52 through the switch connection cable 54.

In addition, the control circuit 57 is connected with the high-frequency driving circuit 55 and the operation display panel 56. The operation signals from the foot switch 52 and the operation display panel 56 are inputted to the control circuit 57, and the control circuit 57 controls the high-frequency driving circuit 55 and the operation display panel 56. The foot switch 52 is provided with a first pedal switch 58 and a second pedal switch 59. The control circuit 57 of the handpiece driving apparatus 51 and the control circuit 43 of the perfusion pump unit 34 are connected to each other through a communication cable 60 such that signals can be bi-directionally transmitted.

As shown in FIG. 12, the handpiece 50 is configured of an ultrasonic treatment instrument unit 61 and a high-frequency treatment instrument unit 62.

As shown in FIGS. 12 and 14, the ultrasonic treatment instrument unit 61 includes a generally cylindrical case 63 which is made of resin, and an ultrasonic transducer and a horn, not shown, provided in the case 63. On the distal end side of the horn is mounted an ultrasonic probe 64 for transmitting ultrasonic vibration. On the distal end side of the ultrasonic probe 64 is formed a treatment portion 65 for treating a living tissue.

As shown in FIG. 14, a C-ring 66 as a detachable member is provided on the distal end side of the case 63. A sheath unit 67 is also provided on the distal end side of the case 63, as shown in FIG. 12. The sheath unit 67 is configured of a sheath main body 68, a C-ring receiving member 69 as a detachable member, which is integrally attached to the sheath main body 68, and a sheath 70 integrally attached to the sheath main body 68. The sheath 70 has a cylindrical shape covering the ultrasonic probe 64. In this embodiment, the sheath unit 67 can be detachably coupled with the case 63 using the C-ring 66 and the C-ring receiving member 69. The sheath main body 68 has a large diameter portion 71 and a small diameter portion 72. The small diameter portion 72 has on the outer peripheral surface thereof engaging grooves 73, 74, which configure a positioning mechanism, formed throughout the periphery. The positioning mechanism, as described later, is a mechanism for selectively positioning an active electrode 83 with respect to the ultrasonic probe 64. Furthermore, the small diameter portion 72 has on the distal end side thereof a guide groove 75 formed extendedly in parallel with a central axis of the ultrasonic probe 64.

As shown in FIGS. 12 and 14, the high-frequency treatment instrument unit 62 has a generally cylindrical operation portion 76. The operation portion 76 incorporates a compression coil spring 77 and an engaging pin 78 biased toward the central axis of the operation portion 76 by the compression coil spring 77. The compression coil spring 77 and the engaging pin 78 function as a positioning mechanism.

The operation portion 76 also has a guide pin 79 provided in a projecting manner in the inner peripheral direction. The guide pin 79 is shaped to engage with the guide groove 75 of the ultrasonic treatment instrument unit 61. The operation portion 76 is provided on the distal end side thereof with an insertion portion 80 having a bore, i.e. an insertion path, through which the sheath 70 of the ultrasonic treatment instrument unit 61 can be inserted.

The insertion portion 80 is made of an electrical insulating resin member or the like. As shown in FIG. 14, a conductive wire 81 made of a metallic member is provided in the insertion portion 80. In addition, one end of the output connection cable 53 is connected to the rear end side of the insertion portion 80 such that a conductive wire 82 of the output connection cable 53 and the conductive wire 81 are connected to each other. On the distal end side of the conductive wire 80 is provided the active electrode 83 made of a member such as metal. The active electrode 83 is connected to the conductive wire 81, covered with an insulating member 84 made of a resin member or the like. In addition, the active electrode 83 has a treatment surface 85 exposed only in the outer peripheral direction of the insertion portion 80. As shown in FIG. 13, a lot of square pyramid-shaped projections are formed on the treatment surface 85 as the treatment portion.

(Working)

Description will be made on the case where a living tissue is treated using the treatment system 1B for surgery according to the present embodiment. First, the arthroscope apparatus 2, the treatment apparatus 49 for surgery, and the perfusion apparatus 4 are placed in a surgery room, as shown in FIG. 10. That is, similarly to the first embodiment, the arthroscope 6 is inserted in the articulation 5 such as the knee, the shoulder, or the hip joint of the patient through the first cannula 9. Furthermore, the handpiece 50 is inserted in the articulation 5 through the second cannula 15. One end of the liquid feeding tube 33 is connected to the first cannula 9 and one end of the drainage tube 35 is connected to the second cannula 15.

Then, similarly to the first embodiment, perfusion in the articulation 5 is performed by the perfusion apparatus 4. As a result, inside of the articulation 5 becomes an inflated state by the constant pressure due to the perfusion liquid such as normal saline, which enables excellent observation with the arthroscope 6.

The handpiece 50 is configured of the ultrasonic treatment instrument unit 61 and the high-frequency treatment instrument unit 62, and is assembled as shown in FIG. 14. That is, the sheath 70 of the ultrasonic treatment instrument unit 61 is inserted into the bore of the insertion portion 80 of the high-frequency treatment instrument unit 62. The engaging pin 78 as the positioning mechanism of the high-frequency treatment instrument unit 62 is engaged with an engaging groove 74 as the positioning mechanism of the ultrasonic treatment instrument unit 61. The engaging pin 78 is biased toward the central axis of the operation portion 76 by the compression coil spring 77. As a result, when the engaging pin 78 is engaged with the engaging groove 74, appropriate clicking feel can be obtained. In addition, the high-frequency treatment instrument unit 62 is positioned such that the position in the central axis direction of the ultrasonic probe 64 is fixed with respect to the ultrasonic treatment instrument unit 61. Furthermore, in the state where the ultrasonic treatment instrument unit 61 and the high-frequency treatment instrument unit 62 are assembled together, the guide pin 79 of the high-frequency treatment instrument unit 62 is engaged with the guide groove 75 of the ultrasonic treatment instrument unit 61. As a result, the high-frequency treatment instrument unit 62 cannot rotate around the central axis of the ultrasonic probe 64 with respect to the ultrasonic treatment instrument unit 61.

FIG. 15 is an exterior view of the handpiece 50 in the state where the engaging pin 78 is engaged with the engaging groove 74 as shown in FIG. 14. In the case shown in FIG. 15, the treatment portion 65 of the ultrasonic treatment instrument unit 61 projects toward the distal end side of the handpiece 50 further than the treatment surface 85 of the high-frequency treatment instrument unit 62. In this state, treatment with the treatment portion 65 of the ultrasonic treatment instrument unit 61 can be performed under excellent observation with the arthroscope 6.

In addition, when the high-frequency treatment instrument unit 62 is moved toward the distal end side (treatment portion side) with respect to the ultrasonic treatment instrument unit 61 from the states shown in FIGS. 14 and 15, engagement between the engaging pin 78 and the engaging groove 74 is released, and the engaging pin 78 is engaged with the engaging groove 73, which results in the state shown in FIG. 16. At this time, the treatment surface 85 of the high-frequency treatment instrument unit 62 advances to the same position as that of the treatment portion 65 of the ultrasonic treatment instrument unit 61. In this state, treatment with the treatment surface 85 of the high-frequency treatment instrument unit 62 can be performed under excellent observation with the arthroscope 6.

Then, treatment is performed on the living tissue by the treatment apparatus 49 for surgery which includes the above-described handpiece 50.

First, description will be made on the treatment with the treatment portion 65 of the ultrasonic treatment instrument unit 61. In this case, in the handpiece 50, the ultrasonic treatment instrument unit 61 and the high-frequency treatment instrument unit 62 are positioned in the state as shown in FIG. 15. Similarly to the first embodiment, when the foot switch 12 is turned on, the ultrasonic probe 64 generates ultrasonic vibration, and the living tissue in contact with the treatment portion 65 of the ultrasonic probe 64 is treated by the ultrasonic vibration.

Next, the high-frequency treatment instrument unit 62 is moved toward the distal end side (treatment portion side) with respect to the ultrasonic treatment instrument unit 61, to obtain the state shown in FIG. 16. In this state, the treatment with the treatment portion 85 as the treatment surface of the high-frequency treatment instrument unit 62 can be performed under excellent observation with the arthroscope 6.

In this case, the output level of the high-frequency output is preset through the operation display panel 56 of the handpiece driving apparatus 51. When treatment is performed with high-frequency output, the treatment portion 85 is brought close to or brought into contact with the region to be treated of the living tissue. When the footswitch 52 is turned on, the operation signal from the foot switch 52 is inputted to the control circuit 57, and the high-frequency driving circuit 55 supplies high-frequency current to the active electrode 83 through the conductive wire 82 of the output connection cable 53 and the conductive wire 81. As a result, the living tissue located close to or in contact with the treatment portion 85 is treated with the high-frequency current.

Note that what is called monopolar high-frequency output may be performed, in which a counter electrode plate (attached on the body surface of the patient and connected to the handpiece driving apparatus 51), not shown, is used as a return electrode. Alternatively, what is called bipolar high-frequency output may be performed, in which the ultrasonic probe 64 made of a metallic material is connected to the handpiece driving apparatus 51 and the ultrasonic probe 64 is used as a return electrode.

Note that, when the first pedal switch 58 of the foot switch 52 is turned on, the high-frequency driving circuit 55 is controlled to supply to the handpiece 50 a cut output at the output level set through the operation display panel 56. When the second pedal switch 59 of the foot switch 52 is turned on, the high-frequency driving circuit 55 is controlled to supply to the handpiece 50 a coagulation output at the output level set through the operation display panel 56. The output waveform of the cut output is a sine wave, and the output waveform of the coagulation output is a burst wave. Note that the active electrode 83 in the shape shown in FIG. 13 is suitable for vaporization and hemostasis of the ligament or the soft tissue in the articulation 5.

Next, when the operator desires to perform the treatment with ultrasonic output, the operator has only to move the high-frequency treatment instrument unit 62 toward the rear end side with respect to the ultrasonic treatment instrument unit 61 in the state where the handpiece 50 is inserted in the articulation 5 and obtain the state shown in FIG. 15. That is, one handpiece 50 enables both the treatment with ultrasonic output and the treatment with high-frequency output.

Alternatively, the ultrasonic treatment instrument unit 61 and the high-frequency treatment instrument unit 62 may be used separately in the state where the ultrasonic treatment instrument unit 61 and the high-frequency treatment instrument unit 62 are not assembled together, i.e., the state shown in FIG. 12. In this case, the bore of the insertion portion 80 of the high-frequency treatment instrument unit 62 is connected to the one end of the drainage tube 35, and thus the bore of the insertion portion 80 can be used as a drainage conduit.

Note that, when the treatment with ultrasonic output is performed, similarly to the first embodiment, white turbidity appears in the perfusion liquid, which makes it difficult to ensure the field of view of the arthroscope 6 in some cases.

Furthermore, when the treatment with high-frequency output is performed, the perfusion liquid in the vicinity of the active electrode 83 is heated by the high-frequency current and numerous air bubbles are thereby generated in the perfusion liquid, which makes it difficult to ensure the field of view of the arthroscope 6 in some cases. Note that, as the output level of the high-frequency output becomes higher, a larger number of air bubbles are generated. As a result, the field of view in the perfusion liquid is more severely obstructed. In addition, the air bubbles tend to be generated in larger number in the cut output than in the coagulation output.

In the present embodiment, similarly to the first embodiment, the control circuit 29 of the handpiece driving apparatus 11 and the control circuit 43 of the perfusion pump unit 34 are connected to each other through the communication cable 44 which can bi-directionally transmit signals. In addition, the control circuit 57 of the handpiece driving apparatus 51 and the control circuit 43 of the perfusion pump unit 34 are connected to each other through the communication cable 60 which can bi-directionally transmit signals. The control circuit 29 sends to the control circuit 43 the signal indicating the output state of the ultrasonic output. In response to the signal, the control circuit 43 controls the liquid feeding pump driving circuit 39 and the drainage valve driving circuit 40 in conjunction with the output state of the ultrasonic output. In addition, the control circuit 57 sends to the control circuit 43 the signal indicating the output state of the high-frequency output. In response to the signal, the control circuit 43 controls the liquid feeding pump driving circuit 39 and the drainage valve driving circuit 40 in conjunction with the output state of the high-frequency output.

As a result, at the time of the treatment with ultrasonic output, even if white turbidity appears in the perfusion liquid, the field of view is rapidly restored similarly to the first embodiment.

Note that FIGS. 17A to 17E and FIGS. 18A to 18E show examples of time charts showing the output state of high-frequency output and the action of the perfusion pump unit 34. FIGS. 17A to 17E are time charts in the case where the handpiece 50 is driven with coagulation output by operating the second pedal switch 59. FIGS. 18A to 18E are time charts in the case where the handpiece 50 is driven with cut output by operating the first pedal switch 58.

In the case shown in FIGS. 17A to 17E, control similar to that in the case shown in FIG. 7 in the first embodiment is performed by the perfusion pump unit 34. In the case shown in FIGS. 18A to 18E, control similar to that in the case shown in FIG. 8 in the first embodiment is performed by the perfusion pump unit 34. As a result, even in the case where the perfusion liquid in the vicinity of the active electrode 83 is heated by the high-frequency current and numerous air bubbles are thereby generated, the field of view is rapidly restored.

In the case shown in FIGS. 18A to 18E where a larger number of air bubbles are generated than in the case shown in FIGS. 17A to 17E, the amount of perfusion during the high-frequency output is increased more than in the case shown in FIGS. 17A to 17E. As a result, even in the state where many air bubbles are generated by cut output, the field of view is restored as rapidly as in the case shown in FIGS. 17A to 17E. In addition, when the treatment with high-frequency output is performed, the perfusion liquid is heated and the living tissue contacted the perfusion liquid is influenced by the heat in some cases. Since the perfusion amount during high-frequency output is increased in the present embodiment, the perfusion liquid in the articulation 5 is efficiently cooled. Thus, the influence of heat on the living tissue can be reduced.
(Effect)

As described above, with the treatment system 1B for surgery according to the present embodiment, similarly to the first embodiment, the field of view is rapidly restored even in the case where white turbidity appears in the perfusion liquid due to the treatment with ultrasonic output.

In addition, even when numerous air bubbles are generated in the perfusion liquid due to the treatment with high-frequency output, the field of view is rapidly restored. In addition, during the treatment with high-frequency output, the perfusion liquid in the articulation 5 is efficiently cooled. Accordingly, the influence of heat on the living tissue can be reduced.

Furthermore, the single handpiece 50 enables both the treatment with ultrasonic output and the treatment with high-frequency output. As a result, there is no need to prepare a plurality of kinds of treatment instruments, which provides excellent economical performance. Furthermore, the operator does not have to change the treatment instrument (extract and insert the treatment instrument from and into the articulation 5) depending on whether the treatment is performed with ultrasonic output or high-frequency output, which reduces the surgery time.

Fourth Embodiment

Next, a treatment system for surgery according to the fourth embodiment of the present invention will be described.

Figure 20:
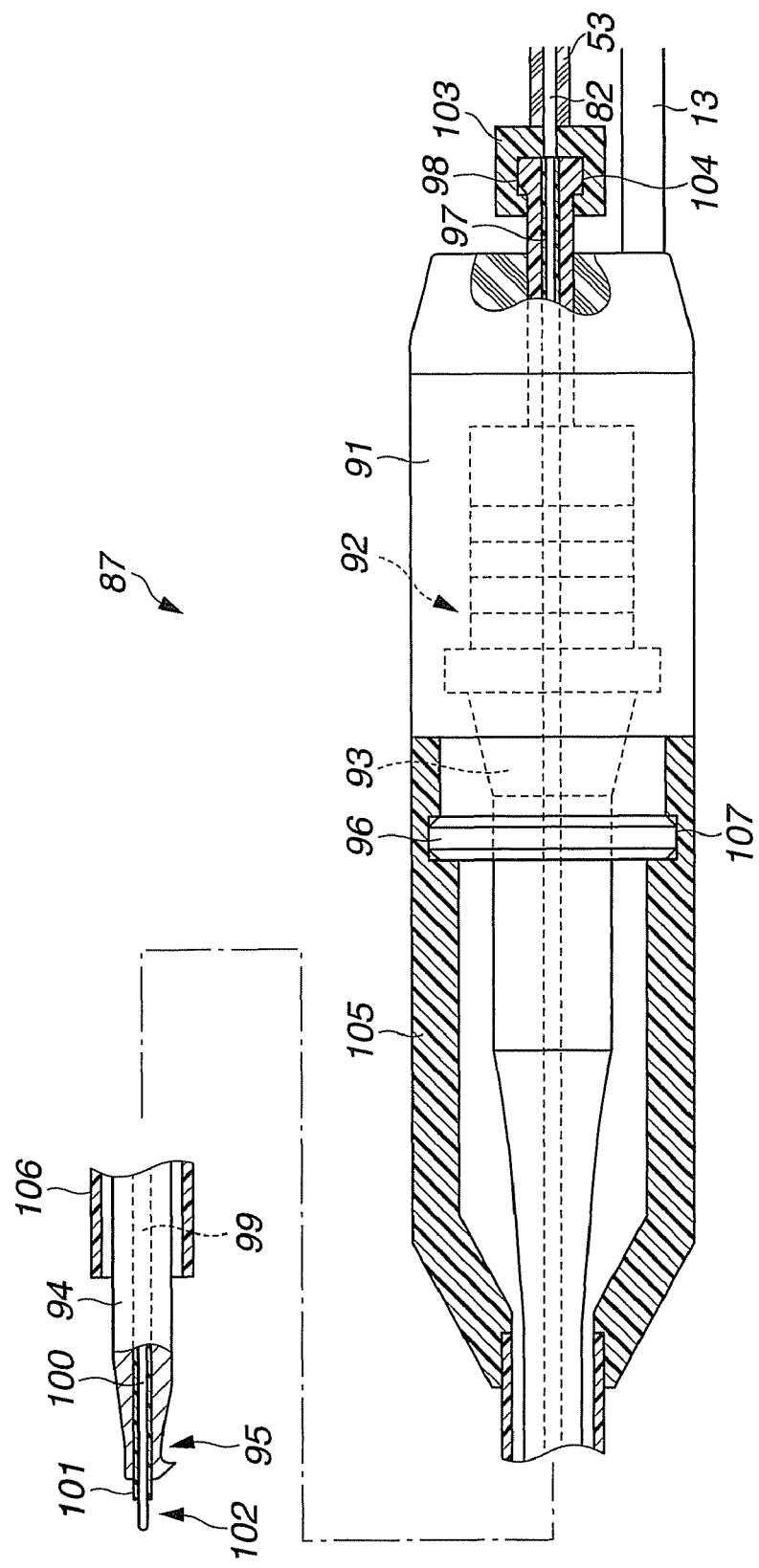
FIG. 20 is a cross-sectional view of the handpiece.
Figure 21:
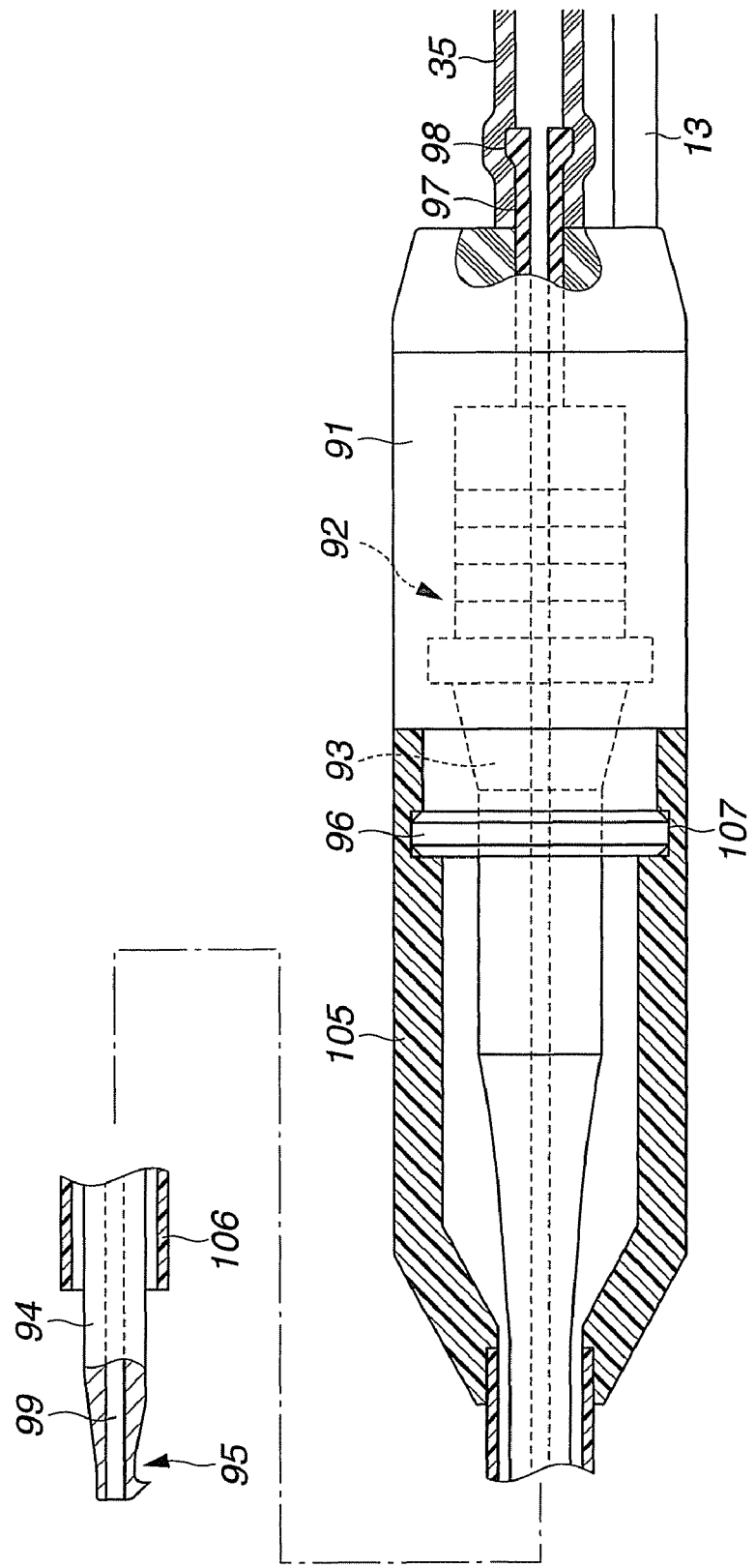
FIG. 21 is a view for describing a state of use of the handpiece.

FIGS. 19 to 21 are block diagrams showing configurations of a treatment apparatus for surgery and a perfusion apparatus according to the fourth embodiment. FIG. 19 is a configurational view showing a configuration of a handpiece according to the fourth embodiment. FIG. 20 is a cross-sectional view of the handpiece. FIG. 21 is a view for describing a state of use of the handpiece. In the description of the present embodiment, the same components as those in the third embodiment are attached with the same reference numerals and descriptions thereof will be omitted. Only the parts different from those in the third embodiment will be described.
(Configuration)

The present embodiment is different from the third embodiment only in the configuration of the handpiece.

As shown in FIGS. 19 and 20, a handpiece 87 is composed of an ultrasonic treatment instrument unit 88, a high-frequency treatment instrument unit 89, and a sheath unit 90.

The ultrasonic treatment instrument unit 88 includes a generally cylindrical case 91, an ultrasonic transducer 92 and a horn 93 that are provided in the case 91. On the distal end side of the horn 93 is mounted an ultrasonic probe 94 for transmitting ultrasonic vibration. On the distal end side of the ultrasonic probe 94 is formed a treatment portion 95 for treating a living tissue. The treatment portion 95 has the same shape as that of the treatment portion 22 shown in FIG. 4 of the first embodiment. An engaging projection portion 96 as a detachable member is provided on the distal end side of the case 91. In addition, a connection member 97 is provided on the rear end side of the case 91. The connection member 97 has an engaging projection portion 98 formed thereon as a detachable portion. In this embodiment, a channel 99 is formed in the ultrasonic probe 94, the horn 93, the ultrasonic transducer 92, and the connection member 97 in such a manner as to penetrate from the distal end of the ultrasonic probe 94 to the rear end of the connection member 97. In addition, the output connection cable 13 is extended from the rear end side of the case 91.

The high-frequency treatment instrument unit 89 has a linear wire 100 and a tube 101 covering the wire 100. The wire 100 is made of a metallic material, and is relatively flexible. The tube 101 is made of an insulating material such as PTFE. The distal end portion of the wire 100 is exposed from the tube 101 to form a treatment portion 102. On the rear end side of the wire 100 is provided a connection member 103 made of an insulating material. In the connection member 103 is formed an engaging recess portion 104, as a detachable portion, to be engaged with the engaging projection portion 98. The rear end side of the connection member 103 is connected with one end of the output connection cable 53 and the conductive wire 82 of the output connection cable 53 is connected to the rear end side of the wire 100.

The sheath unit 90 is composed of a sheath main body 105, and a sheath 106 integrally mounted to the sheath main body 105. As shown in FIG. 20, an engaging recess portion 107 as a detachable portion is formed in the sheath main body 105. The sheath 106 has a cylindrical shape which covers the ultrasonic probe 94.

(Working)

The handpiece 87 is composed of the ultrasonic treatment instrument unit 88, the high-frequency treatment instrument unit 89, and the sheath unit 90, and is assembled as shown in FIG. 20. First, the ultrasonic probe 94 of the ultrasonic treatment instrument unit 88 is inserted into the bore of the sheath 106 of the sheath unit 90. Then, the engaging projection portion 96 of the ultrasonic treatment instrument unit 88 is engaged with the engaging recess portion 107 in the sheath main body 105. Next, the high-frequency treatment instrument unit 89 is inserted into the channel 99 from the rear end side of the ultrasonic treatment instrument unit 88. Then, the engaging projection portion 98 of the connection member 97 is engaged with the engaging recess portion 104 in the connection member 103. The ultrasonic treatment instrument unit 88, the high-frequency treatment instrument unit 89, and the sheath unit 90 are thus assembled together. At this time, the distal end portions of the wire 100 and the tube 101 are exposed from the distal end of the ultrasonic probe 94, as shown in FIG. 20. In addition, the tube 101 which is made of an insulating material electrically insulates the wire 100 from the ultrasonic probe 94. Note that, by releasing the engagement between the engaging projection portion 98 and the engaging recess portion 104 and the engagement between the engaging projection portion 96 and the engaging recess portion 107, the handpiece 87 can be disassembled into the units 88, 89, and 90.

Treatment is performed on the living tissue with the assembled handpiece 87.

The treatment with ultrasonic output is performed with the treatment portion 95 of the ultrasonic probe 94, similarly to the third embodiment.

The treatment with high-frequency output is performed with the treatment portion 102 of the high-frequency treatment instrument unit 89, similarly to the third embodiment. At this time, what is called monopolar high-frequency output may be performed, in which a counter electrode plate (attached on the body surface of the patient and connected to the handpiece driving apparatus 51), not shown, is used as a return electrode. Alternatively, what is called bipolar high-frequency output may be performed, in which the ultrasonic probe 94 made of a metallic material is connected to the handpiece driving apparatus 51 and the ultrasonic probe 94 is used as a return electrode.

As a result, with the treatment system 1B for surgery according to the present embodiment, both the treatment with ultrasonic output and the treatment with high-frequency output can be performed by the single handpiece 87.

In addition, in the present embodiment, similarly to the third embodiment, the control circuit 43 of the perfusion pump unit 34 controls the liquid feeding pump driving circuit 39 and the drainage valve driving circuit 40 in conjunction with the output state of the ultrasonic output or the high-frequency output. Accordingly, similarly to the third embodiment, during the treatment with ultrasonic output or treatment with high-frequency output, the obstructed field of view is rapidly restored.

Note that the treatment with ultrasonic output may be performed in the state where the high-frequency treatment instrument unit 89 is not assembled. At that time, the one end of the drainage tube 35 is connected to the connection member 97, as shown in FIG. 21, and the channel 99 of the ultrasonic treatment instrument unit 88 may be used as a drainage conduit.

Furthermore, also the handpiece 87 according to the present embodiment may be provided with a positioning mechanism, as described in the third embodiment, for selectively positioning the active electrode with respect to the ultrasonic probe 94.

(Effect)

With the treatment system for surgery according to the present embodiment, the same effects as those in the third embodiment can be obtained.

Modified Example of the Fourth Embodiment

Figure 22:
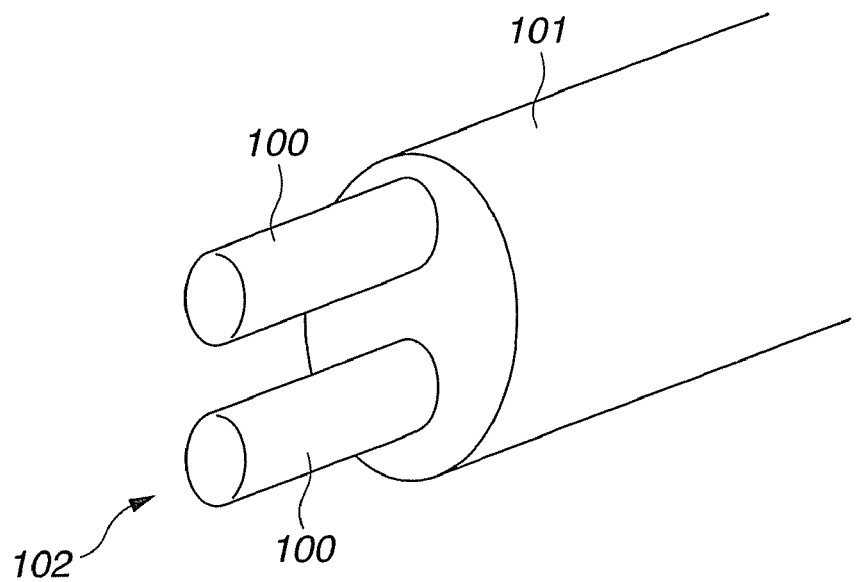
FIG. 22 is a perspective view of an active electrode of a high-frequency treatment instrument unit according to a modified example of the fourth embodiment.
Figure 23:
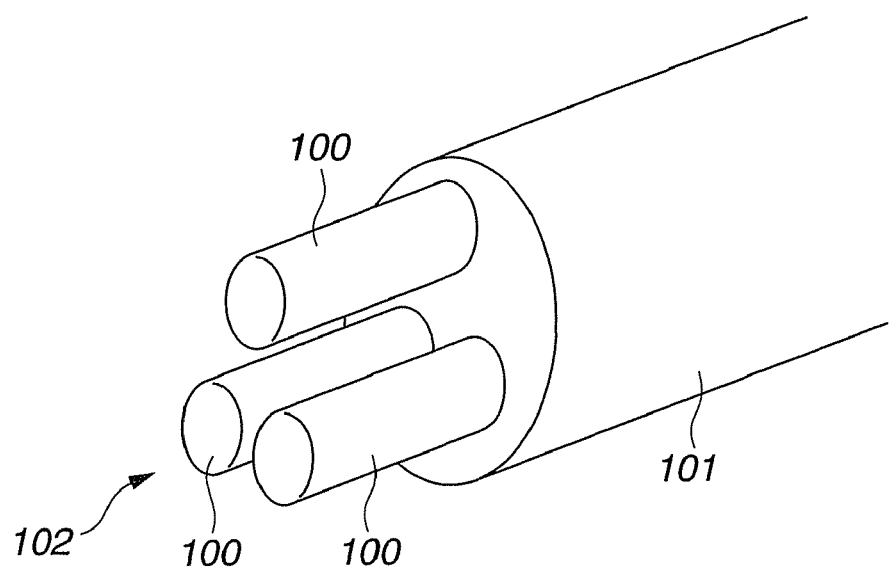
FIG. 23 is a perspective view of another example of the active electrode of the high-frequency treatment instrument unit according to the modified example of the fourth embodiment.
Figure 24:
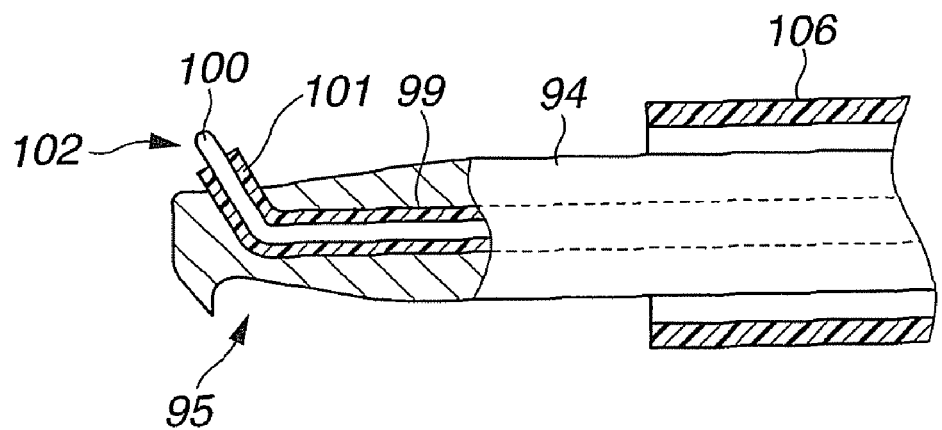
FIG. 24 is a partial cross-sectional view of a treatment portion according to the modified example of the fourth embodiment.
Figure 25:
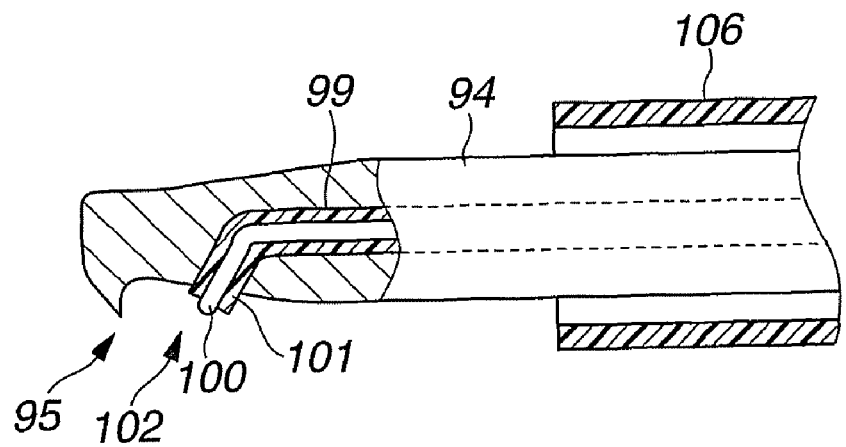
FIG. 25 is a partial cross-sectional view of another example of the treatment portion according to the modified example of the fourth embodiment.
Figure 26:
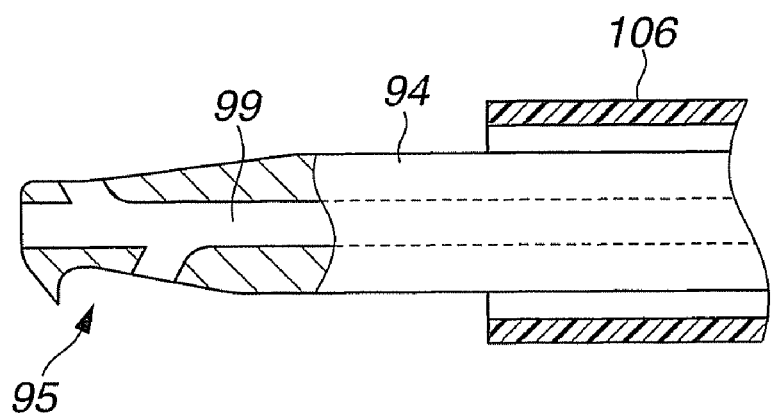
FIG. 26 is a partial cross-sectional view of yet another example of the treatment portion according to the modified example of the fourth embodiment.
Figure 27:
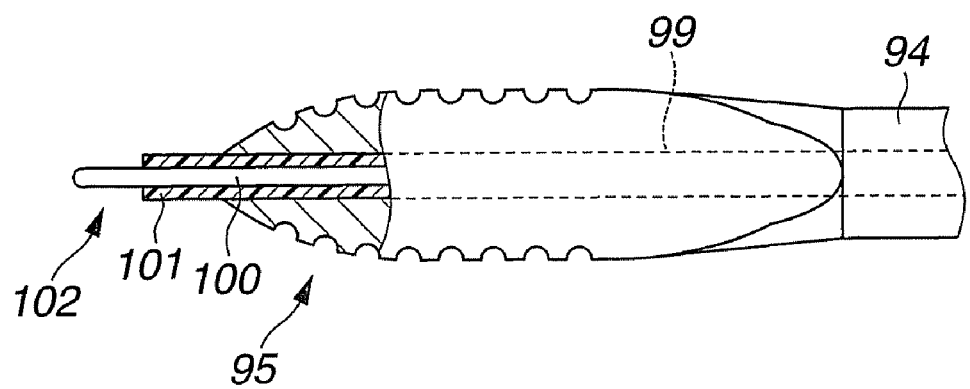
FIG. 27 is a partial cross-sectional view of further yet another example of the treatment portion according to the modified example of the fourth embodiment.

FIGS. 22 to 27 are views describing the modified examples of the fourth embodiment. FIG. 22 is a perspective view of an active electrode of the high-frequency treatment instrument unit according to the modified example of the fourth embodiment. FIG. 23 is a perspective view of another example of the active electrode of the high-frequency treatment instrument unit according to the modified example of the fourth embodiment. FIG. 24 is a partial cross-sectional view of a treatment portion according to the modified example of the fourth embodiment. FIG. 25 is a partial cross-sectional view of another example of the treatment portion according to the modified example of the fourth embodiment. FIG. 26 is a partial cross-sectional view of yet another example of the treatment portion according to the modified example of the fourth embodiment. FIG. 27 is a partial cross-sectional view of further yet another example of the treatment portion according to the modified example of the fourth embodiment.

FIGS. 22 and 23 show different configurations of the treatment portion 102 of the high-frequency treatment instrument unit 89. In FIG. 22, two wires 100 are provided. In FIG. 23, three wires 100 are provided. In these modified examples, high-frequency current may be selectively applied to the two or three wires 100.

FIGS. 24, 25, and 26 show different configurations of the channel 99 formed on the distal end side of the ultrasonic probe 94. In FIG. 24, the extremity of the channel 99 is open in the direction opposite to that of the treatment portion 95 of the ultrasonic probe 94. In FIG. 25, the extremity of the channel 99 is open in the same direction as that of the treatment portion 95 of the ultrasonic probe 94. In FIG. 26, the extremities of the channel 99 are open in three directions.

In these examples, the wire 100 is relatively flexible, so that the wire 100 is insertable through the channel 99 having a curved path as shown in FIG. 24 or FIG. 25.

In addition, if the wire 100 has previously or inherently a tendency to bending, or by giving the tendency to bending to the wire 100, the treatment portion shown in FIG. 26 can use the wire 100 by making the wire project from an opening formed in the direction in which the wire bends.

Note that, when treatment is performed with the handpiece 87 having the treatment portions 95, 102 as shown in FIG. 25, the treatment with ultrasonic output and the treatment with high-frequency output may be performed at the same time. This makes it possible to shave a living tissue while controlling the bleeding. In addition, the treatment portion 102 may be configured to be projectable and retractable from and into the opening of the channel 99, or to be fixable at an arbitrary projecting position.

In the treatment portion shown in FIG. 27, the treatment portion 95 of the ultrasonic probe 94 has a different shape. The treatment portion in FIG. 27 has the same shape as that of the treatment portion 22 shown in FIG. 5 in the first embodiment. The channel 99 is formed along the central axis of the treatment portion, and the treatment portion 102 is inserted through the channel 99.

The treatment system for surgery according to each of the embodiments and the modified example includes the handpiece driving apparatus, the perfusion apparatus which perfuses the liquid in the body cavity and is capable of adjusting the pressure in the body cavity, and the control section which controls the pressure in the body cavity to a different level in conjunction with the output state of the handpiece driving apparatus and changes the flow rate of the perfusion liquid. Accordingly, the treatment system for surgery described above can solve such a problem that it takes long until the field of view is restored if a conventional perfusion pump is used when the field of view is obstructed by the air bubbles or the like generated in the perfusion liquid due to the use of the treatment instrument in endoscopic surgery such as arthroscopic surgery. That is, with the treatment system for surgery according to each of the embodiments and the modified example, an excellent field of view can be always ensured when the treatment instrument such as the high-frequency treatment instrument is used in the endoscopic surgery in the body cavity using the perfusion liquid.

The present invention is not limited to the above-described embodiments and various changes and modifications thereof are possible without departing from the scope of the present invention.

What is claimed is:

1. A treatment system for surgery comprising:
 a handpiece driving apparatus for supplying electric energy to a handpiece, the handpiece including a treatment portion insertable into a body cavity;
 a perfusion apparatus for perfusing liquid in the body cavity, the perfusion apparatus being capable of adjusting pressure in the body cavity; and
 a control section for receiving a signal indicative of an output state of the handpiece driving apparatus, and for controlling the pressure in the body cavity to a different level and changing a flow rate of the liquid in conjunction with the output state of the handpiece driving apparatus, by controlling the perfusion apparatus in accordance with the received signal such that a pressure level in the body cavity when the handpiece is driven is higher than a pressure level in the body cavity when the handpiece is not driven, and such that the flow rate of the liquid when the handpiece is driven is larger than the flow rate of the liquid when the handpiece is not driven.

2. The treatment system for surgery according to claim 1, wherein
 the handpiece includes an ultrasonic transducer and an ultrasonic probe, and
 the handpiece driving apparatus includes an ultrasonic transducer driving circuit for driving the ultrasonic transducer.

3. The treatment system for surgery according to claim 2, wherein
 the handpiece further includes an active electrode to which high-frequency current is supplied, and
 the handpiece driving apparatus includes a high-frequency driving circuit for supplying high-frequency current to the active electrode.

4. The treatment system for surgery according to claim 3, wherein the handpiece includes a positioning mechanism for selectively positioning the active electrode with respect to the ultrasonic probe.

5. The treatment system for surgery according to claim 3, wherein the ultrasonic probe includes a channel penetrating from a rear end to a distal end of the ultrasonic probe, and the active electrode is insertable into the channel.

6. The treatment system for surgery according to claim 1, wherein
 the handpiece includes an active electrode to which high-frequency current is supplied, and
 the handpiece driving apparatus includes a high-frequency driving circuit for supplying high-frequency current to the active electrode.

7. The treatment system for surgery according to claim 1, wherein the perfusion apparatus includes: a liquid source of the liquid; a liquid feeding conduit connected to the liquid source; a liquid feeding pump for pumping out the liquid in the liquid feeding conduit; a drainage conduit; a drainage valve for opening and closing the drainage conduit; and a pressure sensor for monitoring the pressure in the body cavity.

8. The treatment system for surgery according to claim 1, further comprising a switch capable of driving the control section to change a flow rate of the liquid, even in a state where the handpiece driving apparatus is not supplying the electric energy to the handpiece.

9. A control method of a treatment system for surgery by a control section, the control method comprising:
 controlling a perfusion apparatus, by the control section, in accordance with an output state of a handpiece driving apparatus for supplying electric energy to a handpiece having a treatment portion insertable into a body cavity, and based on pressure detected by a pressure sensor for monitoring pressure in the body cavity to perform feeding and drainage of a liquid such that a pressure level in the body cavity when the handpiece is driven is higher than a pressure level in the body cavity when the handpiece is not driven, and such that a flow rate of the liquid when the handpiece is driven is larger than the flow rate of the liquid when the handpiece is not driven.

10. The control method of the treatment system for surgery according to claim 9, wherein the control section controls the perfusion apparatus such that a flow rate of the feeding and drainage of the liquid when the handpiece is driven is larger than a flow rate of the feeding and drainage of the liquid when the handpiece is not driven.

11. The control method of the treatment system for surgery according to claim 10, wherein the control section controls the perfusion apparatus to perform the feeding and drainage of the liquid in response to operation of a predetermined switch even in a state where the handpiece driving apparatus is not supplying the electric energy to the handpiece.

12. The control method of the treatment system for surgery according to claim 9, wherein the control section controls the perfusion apparatus to perform the feeding and drainage of the liquid in response to operation of a predetermined switch even in a state where the handpiece driving apparatus is not supplying the electric energy to the handpiece.

* * * * *